US006630573B1

(12) United States Patent
Walker et al.

(10) Patent No.: US 6,630,573 B1
(45) Date of Patent: Oct. 7, 2003

(54) TAU-CONOTOXIN PEPTIDES

(75) Inventors: Craig Walker, Salt Lake City, UT (US); Reshma Shetty, Salt Lake City, UT (US); Baldomero M. Olivera, Salt Lake City, UT (US); David Hooper, Salt Lake City, UT (US); Richard Jacobsen, San Francisco, CA (US); Doug Steele, Salt Lake City, UT (US); Robert Jones, Salt Lake City, UT (US)

(73) Assignees: Cognetix, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/497,491

(22) Filed: Feb. 4, 2000

Related U.S. Application Data

(60) Provisional application No. 60/118,642, filed on Feb. 4, 1999.

(51) Int. Cl.[7] .................. A61K 38/08; A61K 38/17; C07K 7/08; C07K 14/00; C07K 14/435
(52) U.S. Cl. .................. 530/328; 530/326; 530/402
(58) Field of Search .................. 514/15, 14, 13, 514/21, 11; 530/300, 326, 327, 328, 402, 333; 424/185.1

(56) References Cited

U.S. PATENT DOCUMENTS

| | | |
|---|---|---|
| 4,447,356 A | 5/1984 | Olivera et al. |
| 5,231,011 A | 7/1993 | Hillyard et al. |
| 5,432,155 A | 7/1995 | Olivera et al. |
| 5,514,774 A | 5/1996 | Olivera et al. |
| 5,591,821 A | 1/1997 | Olivera et al. |
| 5,670,622 A | 9/1997 | Shon et al. |
| 5,672,682 A | 9/1997 | Terlau et al. |
| 5,719,264 A | 2/1998 | Shon et al. |
| 5,739,276 A | 4/1998 | Shon et al. |
| 5,889,147 A | 3/1999 | Cruz et al. |
| 5,969,096 A | 10/1999 | Shon et al. |
| 5,990,295 A | 11/1999 | Shon et al. |
| 6,077,934 A | 6/2000 | Jacobsen et al. |

OTHER PUBLICATIONS

Savarin, P. et al. "Three–Dimensional Structure of k–Conotoxin PVIIA, a Novel Potassium Channel–Blocking Toxin from Cone Snails", Biochemistry; 1998, 37:5407–5416.
Norton, R. et al. "The Cystine Knot Structure of Ion Channel Toxins and Related Polypeptides", Toxicon; 1998, vol. 36, No. 11: 1573–1583.
Gray, W.R. et al. "Peptides Toxins from Conus geographus Venom", The Journal of Biological Chemistry;1981: vol. 256 No. 10, 4734–4740.
Abstract, "Animal Venoms: From Neurotoxins to Clotting Factors," 20th Blankenese Conference, Hamburg–Blankenese, Germany, May 10–14, 2000.
Myers, R.A. et al. (1993). "Conus Peptides as Chemical Probes for Receptors and Ion Channels," *Chem. Rev.* 93:1923–1936.
Olivera, B.M. et al. (1985). "Peptide Neurotoxins from Fish–Hunting Cone Snails," *Science* 230:1338–1343.
Olivera, B.M. et al. (1990). "Diversity of Conus Neuropeptides," *Science* 249:257–263.
Rigby, A.C. et al. (1999). "A conotoxin from *Conus textile* with unusual posttranslational modifications reduces presynaptic $Ca^{2+}$ influx," *Proc. Nat. Acad. Sci. USA* 96:5758–5763.
Walker, C.S. et al. (1999). "The T–superfamily of Conotoxins," *J. Biol. Chem.* 274(43):30664–30671.

*Primary Examiner*—Karen Cochrane Carlson
*Assistant Examiner*—Samuel Liu
(74) *Attorney, Agent, or Firm*—Rothwell, Figg, Ernst & Manbeck

(57) ABSTRACT

The invention relates to relatively short peptides (termed τ-conotoxins herein), about 10–25 residues in length, which are naturally available in minute amounts in the venom of the cone snails or analogous to the naturally available peptides, and which preferably include two disulfide bonds.

8 Claims, No Drawings

TAU-CONOTOXIN PEPTIDES

CROSS-REFERENCE TO RELATED APPLICATION

The present application is related to U.S. provisional patent application Ser. No. 60/118,642 filed on Feb. 4, 1999, incorporated herein by reference.

This invention was made with Government support under Grant No. PO 1 GM48677 awarded by the National Institute of General Medical Sciences, National Institutes of Health, Bethesda, Md. The United States Government has certain rights in the invention.

BACKGROUND OF THE INVENTION

The invention relates to relatively short peptides (termed τ-conotoxins herein), about 10–20 residues in length, which are naturally available in minute amounts in the venom of the cone snails or analogous to the naturally available peptides, and which preferably include two disulfide bonds.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these peptides are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ- and ω-conotoxins which target nicotinic acetylcholine receptors, muscle sodium channels, and neuronal calcium channels, respectively (Olivera et at., 1985). Conopressins, which are vasopressin analogs, have also been identified (Cruz et al. 1987). In addition, peptides named conantokins have been isolated from *Conus geographus* and *Conus tulipa* (Mena et al., 1990; Haack et al., 1990).

Chronic or intractable pain, which may result from degenerative conditions or debilitating diseases, is currently treated with a variety of analgesic compounds, often opioid compounds such as morphine. Likewise, neuropathic pain, typically a chronic condition attributable to injury or partial transection of a peripheral nerve, is also conventionally treated with opioid compounds such as morphine.

Conventional therapies for pain produce analgesia—a loss of sensitivity to pain without the loss of consciousness. Opioid compounds have been used widely to produce analgesia, including plant-derived opioids such as morphine, and endogenous opioids such as met- and leu-enkephalins, as well as beta-endorphin.

Opioid compounds, while effective in producing analgesia for many types of pain, may induce tolerance in some patients. When a patient becomes tolerant, increasing doses of the opioid are required to produce the desired analgesic effect. In addition, these compounds frequently result in a physical dependence in patients, and may have side effects at high doses.

The analgesic effects and adverse actions of various N-methyl-D-aspartate (NMDA) receptor antagonists has been shown to vary depending on the site of action and potency of the drug. For example, NMDA receptor antagonists acting at the ion channel in a noncompetitive manner (e.g., MK-801 and phenylcyclidine (PCP)) or competitive inhibitors, show analgesic activity but show motor impairment at equivalent doses. Glycine B-site NMDA antagonists appear to have analgesic activity at doses that do not impair motor function. Conantokins, which are polyamine-site NMDA antagonist compounds have analgesic effects at doses which do not produce overt side effects (PCT published application WO 98/03189).

It is desired to provide additional compounds which have analgesic properties.

SUMMARY OF THE INVENTION

The invention relates to relatively short peptides (termed τ-conotoxins herein), about 10–25 residues in length, which are naturally available in minute amounts in the venom of the cone snails or analogous to the naturally available peptides, and which preferably include two disulfide bonds.

More specifically, the present invention is directed to τ-conotoxin peptides having the general formula I:

$Xaa_1$-$Xaa_2$-$Xaa_3$-$Xaa_4$-Cys-Cys-$Xaa_5$-$Xaa_6$-$Xaa_7$-$Xaa_8$-$Xaa_9$-Cys-Cys-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$ (SEQ ID NO:1), wherein $Xaa_1$ is des-$Xaa_1$, Asp, Glu or γ-carboxy-Glu (Gla); $Xaa_2$ is des-$Xaa_2$, Gln, Asn, Glu, Trp (D or L), neo-Trp, halo-Trp or any unnatural aromatic amino acid; $Xaa_3$ is des-$Xaa_3$, Gly, Ala, Asn or Gln; $Xaa_4$ is des-$Xaa_4$, Val, Leu (D or L), Ile, Ala, Gly, Glu, Gla, Asp, Ser, Thr, Phe, Trp (D or L), neo-Trp, halo-Trp (D or L) or any unnatural aromatic amino acid; $Xaa_5$ is Pro, hydroxy-Pro, Gln, Asn, Glu, Gla, Ala, Gly, Lys, Arg, Ile, Val, homoarginine, ornithine, N-methyl-Lys, N,N-dimethyl-Lys, N,N,N-trimethyl-Lys or any unnatural basic amino acid; $Xaa_6$ is Val, Phe, Thr, Ser, Glu, Gla, Asp, Asn, Gln, Ala, Gly, Ile, Leu (D or L) Met, Pro, hydroxy-Pro, Arg, homoarginine, ornithine, Lys, N-methyl-Lys, N,N-dimethyl-Lys, N,N,N-trimethyl-Lys, any unnatural basic amino acid or any unnatural aromatic amino acid; $Xaa_7$ is any Val, Ile, Asn, Leu (D or L), Gln, Gly, Ala, Phe, Glu, Gla, Arg, ornithine, homoarginine, Lys, N-methy-Lys, N,N-dimethyl-Lys, N,N,N-trimethyl-Lys, any unnatural basic amino acid or any unnatural aromatic amino acid; $Xaa_8$ is Ile, Leu (D or L), Met, Thr, Ser, Pro, hydroxy-Pro, Gln, Asp, Glu, Gla, Asn, Arg, homoarginine, ornithine, Lys, N-methy-Lys, N,N-dimethyl-Lys, N,N,N-trimethyl-Lys, Tyr, nor-Tyr, mono-halo-Tyr, di-halo-Tyr, O-sulpho-Tyr, O-phospho-Tyr, nitro-Tyr, any unnatural basic amino acid, any unnatural aromatic amino acid or any unnatural hydroxy containing amino acid; $Xaa_1$ is des-$Xaa_9$, Ala, Gly, Asp, Glu, Gla, Trp (D or L) neo-Trp, halo-Trp (D or L), Lys, N-methy-Lys, N,N-dimethyl-Lys, N,N,N-trimethyl-Lys, Arg, homoarginine, ornithine, Tyr, nor-Tyr, mono-halo-Tyr, di-halo-Tyr, O-sulpho-Tyr, O-phospho-Tyr, nitro-Tyr or any unnatural basic amino acid; $Xaa_{10}$ is des-$Xaa_{10}$, Ile, Leu (D or L), Val, Glu, Gla, Asp, Thr, Ser, Pro, hydroxy-Pro, Trp (D or L), neo-Trp, halo-Trp (D or L), Phe, any unnatural aromatic amino acid or any unnatural hydroxy containing amino acid; $Xaa_1$, is des-$Xaa_{11}$, Gln, Asn, Leu (D or L), Ile, Val, Ala, Gly, Trp (D or L), neo-Trp, halo-Trp (D or L), Arg, homoarginine, ornithine, Lys, N-methy-Lys, N,N-dimethyl-Lys, N,N,N-trimethyl-Lys, any unnatural basic amino acid or any unnatural aromatic amino acid; $Xaa_{12}$ is des-$Xaa_{12}$, Ala, Gly, Phe, Trp (D or L), neo-Trp, halo-Trp (D or L) or any unnatural aromatic amino acid; $Xaa_{13}$ is des-$Xaa_{13}$, Glu, Gla, Asp, Phe or any unnatural aromatic amino acid; $Xaa_{14}$ is des-$Xaa_{14}$, Ile, Val or Leu (D or L); $Xaa_{15}$ is des-$Xaa_{15}$, Thr, Ser, Arg, homoarginine, ornithine, Lys, N-methy-Lys, N,N-dimethyl-Lys, N,N,N-trimethyl-Lys or any unnatural basic amino acid; $Xaa_{16}$ is des-$Xaa_{16}$, Glu, Gla or Asp; $Xaa_{17}$ is des-$Xaa_{17}$, Asn or Gln; $Xaa_{18}$ is des-$Xaa_{18}$, Asp, Glu or Gla; $Xaa_{19}$ is des-$Xaa_{19}$, Phe or any unnatural aromatic amino acid. The C-terminus may contain a free carboxyl group or an amide group. The halo is preferably bromine, chlorine or iodine, more preferably iodine for Tyr and bromine for Trp. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic amino acid, e.g., tetrazolyl derivatives of Gly and Ala.

The present invention is also directed to novel specific τ-conotoxin peptides of general formula I having the formulas:

Phe-Cys-Cys-$Xaa_1$-Val-Ile-Arg-$Xaa_2$-Cys-Cys-$Xaa_3$ (SEQ ID NO:2);

Phe-Cys-Cys-$Xaa_1$-Phe-Ile-Arg-$Xaa_2$-Cys-Cys-$Xaa_3$ (SEQ ID NO:3);

Cys-Cys-Gln-Thr-Phe-$Xaa_2$-$Xaa_3$-Cys-Cys-Gln (SEQ ID NO:4);

$Xaa_4$-Gly-$Xaa_3$-Cys-Cys-$Xaa_5$-$Xaa_6$-Asn-Ile-Ala-Cys-Cys-Ile (SEQ ID NO:5);

Gly-Cys-Cys-Ala-Arg-Leu-Thr-Cys-Cys-Val (SEQ ID NO:6);

Asn-Gly-Cys-Cys-$Xaa_1$-$Xaa_5$-Gln-Met-Arg-Cys-Cys-Thr (SEQ ID NO:7);

Asp-$Xaa_3$-Asn-Ser-Cys-Cys-Gly-$Xaa_6$-Asn-$Xaa_1$-Gly-Cys-Cys-$Xaa_1$-$Xaa_3$ (SEQ ID NO:8);

$Xaa_4$-Gly-$Xaa_3$-Cys-Cys-$Xaa_5$-$Xaa_6$-Asn-Ile-Arg-Cys-Cys-Val (SEQ ID NO:9);

$Xaa_6$-Cys-Cys-$Xaa_6$-Asp-Gly-$Xaa_3$-Cys-Cys-Thr-Ala-Ala-$Xaa_1$-Leu-Thr (SEQ ID NO:10);

Gly-Cys-Cys-$Xaa_6$-Asp-Gly-$Xaa_3$-Cys-Cys-Thr-Ala-Ala-$Xaa_1$-Leu-Thr(SEQ ID NO:11);

Asn-Gly-Cys-Cys-Arg-Ala-Gly-Asp-Cys-Cys-Ser-Arg-Phe-$Xaa_6$-Ile-$Xaa_5$-$Xaa_6$-Asn-Asp-Phe (SEQ ID NO:12);

Asn-Ala-Cys-Cys-Ile-Val-Arg-Gln-Cys-Cys (SEQ ID NO:13);

Asn-Gly-Cys-Cys-Arg-Ala-Gly-Asp-Cys-Cys-Ser (SEQ ID NO:14);

Cys-Cys-$Xaa_1$-Arg-Arg-Leu-Ala-Cys-Cys-Ile-Ile (SEQ ID NO:15);

Cys-Cys-$Xaa_1$-Asn-$Xaa_5$-$Xaa_1$-Cys-Cys-Phe-Ile (SEQ ID NO:16);

Gly-Cys-Cys-Ala-Met-Leu-Thr-Cys-Cys-Val (SEQ ID NO:17);

Leu-Cys-Cys-Val-Thr-$Xaa_6$-Asp-$Xaa_3$-Cys-Cys-$Xaa_6$-$Xaa_3$-$Xaa_3$ (SEQ ID NO:18); and Val-Cys-Cys-Arg-$Xaa_1$-Val-Gln-Asp-Cys-Cys-Ser (SEQ ID NO:19);

wherein $Xaa_1$ is Pro or hydroxy-Pro; $Xaa_2$ is Tyr, mono-halo-Tyr, di-halo-Tyr, O-sulpho-Tyr, O-phospho-Tyr or nitro-Tyr; $Xaa_3$ is Trp or halo-Trp; $Xaa_4$ is Gln or pyro-Glu; $Xaa_5$ is Lys, N-methyl-Lys, N,N-dimethyl-Lys or N,n,N-trimethyl-Lys, $Xaa_6$ is Glu or gamma-carboxy-Glu (Gla); and the C-terminus contains a carboxyl or amide group. The halo is preferably bromine, chlorine or iodine, more preferably iodine for Tyr and bromine for Trp. In addition, the Arg residues may be substituted by Lys, ornithine, homoargine, N-methyl-Lys, N,N-dimethyl-Lys, N,N,N-trimethyl-Lys or any unnatural basic amino acid; the Lys residues may be substituted by Arg, ornithine, homoargine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe and Trp residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic amino acid, e.g., tetrazolyl derivatives of Gly and Ala.

More specifically, the present invention is directed to the following τ-conotoxin peptides of general formula I:

AuVA: SEQ ID NO:2, wherein $Xaa_1$ is Pro, $Xaa_2$ is Tyr and $Xaa_3$ is Trp;

AuVB: SEQ ID NO:3, wherein $Xaa_1$ is Pro, $Xaa_2$ is Tyr and $Xaa_3$ is Trp;

Tx5.1: SEQ ID NO:4, wherein $Xaa_2$ is Tyr and $Xaa_3$ is Trp;

G5.1: SEQ ID NO:5, wherein $Xaa_3$ is Trp, $Xaa_4$ is Gln, $Xaa_5$ is Lys and $Xaa_6$ is Glu;

Qc5.1: SEQ ID NO:6;

PVA: SEQ ID NO:7, wherein $Xaa_1$ is Pro and $Xaa_5$ is Lys;

Im5.1: SEQ ID NO:8, wherein $Xaa_1$ is Pro, $Xaa_3$ is Trp and $Xaa_1$ is Lys;

G5.2: SEQ ID NO:9, wherein $Xaa_3$ is Trp, $Xaa_4$ is Gln, $Xaa_5$ is Lys and $Xaa_6$ is Glu;

Tx5.2a: SEQ ID NO:10, wherein $Xaa_1$ is Pro, $Xaa_3$ is Trp and $Xaa_6$ is Glu;

Tx5.2b: SEQ ID NO:11, wherein $Xaa_1$ is Pro, $Xaa_3$ is Trp and $Xaa_6$ is Glu;

Mr5.1: SEQ ID NO:12, wherein $Xaa_1$ is Lys and $Xaa_6$ is Glu;

Mr5.2: SEQ ID NO:13;

Mr5.3: SEQ ID NO:14;

Ca5.1: SEQ ID NO:15, wherein $Xaa_1$ is Pro;

Ca5.2: SEQ ID NO:16, wherein $Xaa_1$ is Pro and $Xaa_5$ is Lys;

Qc5.2: SEQ ID NO:17;

Gm5.1: SEQ ID NO:18, wherein $Xaa_3$ is Trp and $Xaa_6$ is Glu; and

Gm5.2: SEQ ID NO:19, wherein $Xaa_1$ is Pro.

The C-terminus preferably contains a carboxyl group for the peptides AuVA, AuVB, G5.1, PVA, G5.2, Mr5.2, Mr5.3 and Gm5.1 The C-terminus of the other peptides preferably contains an amide group.

Examples of unnatural aromatic amino acid include, but are not limited to, such as nitro-Phe, 4-substituted-Phe wherein the substituent is $C_1$–$C_3$ alkyl, carboxyl, hyrdroxymethyl, sulphomethyl, halo, phenyl, —CHO, —CN, —SO₃H and —NHAc. Examples of unnatural hydroxy containing amino acid, include, but are not limited to, such as 4-hydroxymethyl-Phe, 4-hydroxyphenyl-Gly, 2,6-dimethyl-Tyr and 5-amino-Tyr. Examples of unnatural basic amino acids include, but are not limited to, N-1-(2-pyrazolinyl)-Arg, 2-(4-piperinyl)-Gly, 2-(4-piperinyl)-Ala, 2-[3-(2S)pyrrolininyl)-Gly and 2-[3-(2S)pyrrolininyl)-Ala. These and other unnatural basic amino acids, unnatural hydroxy containing amino acids or unnatural aromatic amino acids are described in Building Block Index, Version 3.0 (1999 Catalog, pages 4–47 for hydroxy containing amino acids and aromatic amino acids and pages 66–87 for basic amino acids), incorporated herein by reference, by and available from RSP Amino Acid Analogues, Inc., Worcester, Mass. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference.

Optionally, in the peptides of general formula I and the specific peptides described above, the Asn residues may be modified to contain an N-glycan and the Ser and Thr residues may be modified to contain an O-glycan. In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The glycan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1–.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. patent application Ser. No. 09/420,797, filed Oct. 19, 1999 and in PCT Application No. PCT/US99/24380, filed Oct. 19, 1999, both incorporated herein by reference. A preferred glycan is Gal(β1→3)GalNAc(α1→).

Optionally, in the peptides of general formulas I and II and the specific peptides described above, pairs of Cys residues may be replaced pairwise with isosteric lactam or ester-thioether replacements, such as Ser/(Glu or Asp), Lys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The present invention is further directed to propeptides and nucleic acid sequences encoding the propeptides or peptides as described in further detail herein.

SUMMARY OF THE SEQUENCE LISTING

SEQ ID NO:1 is generic formula I for τ-conotoxin peptides. SEQ ID NO:2 is a generic formula for the peptide AuVA. SEQ ID NO:3 is a generic formula for the peptide AuVB. SEQ ID NO:4 is a generic formula for the peptide Tx5.1. SEQ ID NO:5 is a generic formula for the peptide G5.1. SEQ ID NO:6 is a generic formula for the peptide Qc5.1. SEQ ID NO:7 is a generic formula for the peptide PVA. SEQ ID NO:8 is a generic formula for the peptide Im5.1. SEQ ID NO:9 is a generic sequence for the peptide G5.2. SEQ ID NO:10 is a generic sequence for the peptide Tx5.2a. SEQ ID NO:11 is a generic sequence for the peptide Tx5.2b. SEQ ID NO:12 is a generic sequence for the peptide Mr5.1. SEQ ID NO:13 is a generic sequence for the peptide Mr5.2. SEQ ID NO:14 is a generic formula for the peptide Mr5.3. SEQ ID NO:15 is a generic formula for the peptide Ca5.1. SEQ ID NO:16 is a generic formula for the peptide Ca5.2. SEQ ID NO:17 is a generic formula for the peptide Qc5.2. SEQ ID NO:18 is a generic formula for the peptide Gm5.1. SEQ ID NO:19 is a generic formula for the peptide Gm5.2. SEQ ID NO:20 is a DNA sequence coding for the Tx5.1 propeptide. SEQ ID NO:21 is the amino acid sequence of the Tx5.1 propeptide. SEQ ID NO:22 is a DNA sequence coding for the G5.1 propeptide. SEQ ID NO:23 is the amino acid sequence of the G5.1 propeptide. SEQ ID NO:24 is a DNA sequence coding for the Qc5.1 propeptide. SEQ ID NO:25 is the amino acid sequence of the Qc5.1 propeptide. SEQ ID NO:26 is a DNA sequence coding for the Im5.1 propeptide. SEQ ID NO:27 is the amino acid sequence of the Im5.1 propeptide. SEQ ID NO:28 is a DNA sequence coding for the G5.2 propeptide. SEQ ID NO:29 is the amino acid sequence of the G5.2 propeptide. SEQ ID NO:30 is a DNA sequence coding for the Tx5.2 propeptide. SEQ ID NO:31 is the amino acid sequence of the Tx5.2 propeptide. SEQ ID NO:32 is a DNA sequence coding for the Tx5.3 propeptide. SEQ ID NO:33 is the amino acid sequence of the Tx5.3 propeptide. SEQ ID NO:34 is a DNA sequence coding for the Mr5.1 peptide. SEQ ID NO:35 is the amino acid sequence of the Mr5.1 peptide. SEQ ID NO:36 is a DNA sequence coding for the Mr5.2 peptide. SEQ ID NO:37 is the amino acid sequence of the Mr5.2 peptide. SEQ ID NO:38 is a DNA sequence coding for the Mr5.3 propeptide. SEQ ID NO:39 is the amino acid sequence of the Mr5.3 propeptide. SEQ ID NO:40 is a DNA sequence coding for the Ca5.1 propeptide. SEQ ID NO:41 is the amino acid sequence of the Ca5.1 propeptide. SEQ ID NO:42 is a DNA sequence coding for the Ca5.2 propeptide. SEQ ID NO:43 is the amino acid sequence of the Ca5.2 propeptide. SEQ ID NO:44 is a DNA sequence coding for the Qc5.2 propeptide. SEQ ID NO:45 is the amino acid sequence of the Qc5.2 propeptide. SEQ ID NO:46 is a DNA sequence coding for the Gm5.1 propeptide. SEQ ID NO:47 is the amino acid sequence of the Gm5.1 propeptide. SEQ ID NO:48 is a DNA sequence coding for the Gm5.2 propeptide. SEQ ID NO:49 is the amino acid sequence of the Gm5.2 propeptide.

DETAILED DESCRIPTION OF THE PREFERRED EMBODIMENT

The invention relates to relatively short peptides (termed r-conotoxins herein), about 10–25 residues in length, which are naturally available in minute amounts in the venom of the cone snails or analogous to the naturally available peptides, and which preferably include two disulfide bonds.

The present invention, in another aspect, relates to a pharmaceutical composition comprising an effective amount of an τ-conotoxin peptide, a mutein thereof, an analog thereof, an active fragment thereof or pharmaceutically acceptable salts. Such a pharmaceutical composition has the capability of acting as an antagonist for acetylcholine receptors and as analgesic agents for the treatment of pain, including migraine. Thus, the pharmaceutical compositions of the present invention are useful in the treatment of pain (whether acute or chronic), including chronic pain, and neuropathic pain, without undesirable side effects.

The τ-conotoxin peptides described herein are sufficiently small to be chemically synthesized. General chemical syntheses for preparing the foregoing τ-conotoxin peptides are described hereinafter. Various ones of the τ-conotoxin peptides can also be obtained by isolation and purification from specific Conus species using the technique described in U.S. Pat. Nos. 4,447,356 (Olivera et al., 1984); 5,514,774; 5,719,264; and 5,591,821, as well as in PCT published application WO 98/03189, the disclosures of which are incorporated herein by reference.

Although the τ-conotoxin peptides of the present invention can be obtained by purification from cone snails, because the amounts of τ-conotoxin peptides obtainable from individual snails are very small, the desired substantially pure τ-conotoxin peptides are best practically obtained in commercially valuable amounts by chemical synthesis using solid-phase strategy. For example, the yield from a single cone snail may be about 10 micrograms or less of τ-conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active τ-conotoxin peptides depends of course upon correct determination of the amino acid sequence.

The τ-conotoxin peptides can also be produced by recombinant DNA techniques well known in the art. Such techniques are described by Sambrook et al. (1989). A gene of interest (i.e., a gene that encodes a suitable τ-conotoxin peptide) can be inserted into a cloning site of a suitable expression vector by using standard techniques. These techniques are well known to those skilled in the art. The expression vector containing the gene of interest may then be used to transfect the desired cell line. Standard transfection techniques such as calcium phosphate co-precipitation, DEAE-dextran transfection or electroporation may be utilized. A wide variety of host/expression vector combinations may be used to express a gene encoding a conotoxin peptide of interest. Such combinations are well known to a skilled artisan. The peptides produced in this manner are isolated, reduced if necessary, and oxidized to form the correct disulfide bonds.

One method of forming disulfide bonds in the τ-conotoxin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH—MBHA resin support. When the unsubstituted amide is desired, use of a BHA or MBHA resin-is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (dicyclohexylcarbodiimide (DCC), diisopropylcarbodiimide (DIC), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), O-(Benzotriazol-1-yl)-N,N,N',N'-tetramethyluronium tetrafluoroborate (TBTU) in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1 H-benzotriazole-1-yl)-1,1,3,3-tetramethyluronium hexafluorophosphate (HBTU) and diethylisopro-pylethylamine (DIEA). The FMOC protecting group is removed by treatment with a 20% solution of piperidine in dimethylformamide(DMF). Resins are subsequently washed with DMF (twice), followed by methanol and NMP.

Muteins, analogs or active fragments, of the foregoing conotoxin peptides are also contemplated here. See, e.g., Hammerland et al, Eur. J. Pharmacol., 226, pp. 239–244 (1992). Derivative muteins, analogs or active fragments of the conotoxin peptides may be synthesized according to known techniques, including conservative amino acid substitutions, such as outlined in U.S. Pat. Nos. 5,545,723 (see particularly col. 2, line 50—col. 3, line 8); 5,534,615 (see particularly col. 19, line 45—col. 22, line 33); and 5,364,769 (see particularly col. 4, line 55—col. 7, line 26), each herein incorporated by reference.

Pharmaceutical compositions containing a compound of the present invention or its pharmaceutically acceptable salts as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral. The compositions may further contain anti-oxidizing agents, stabilizing agents, preservatives and the like. For examples of delivery methods see U.S. Pat. No. 5,844,077, incorporated herein by reference.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington's Pharmaceutical Sciences*. Typically the active agents of the present invention exhibit their effect at a dosage range from about 0.001 mg/kg to about 250 mg/kg, preferably from about 0.01 mg/kg to about 100 mg/kg of the active ingredient, more preferably from about 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

EXAMPLES

The present invention is described by reference to the following Examples, which are offered by way of illustration and are not intended to limit the invention in any manner. Standard techniques well known in the art or the techniques specifically described below were utilized.

Example 1

Isolation of τ-Conotoxins

Crude venom was extracted from venom ducts (Cruz et al., 1976), and the components were purified as previously described (Cartier et al., 1996). The crude extract from venom ducts was purified by reverse phase liquid chromatography (RPLC) using a Vydac $C_{18}$ semi-preparative column (10×250 mm). Further purification of bioactive peaks was done on a Vydac $C_{18}$ analytical column (4.6×220 mm). The effluents were monitored at 220 nm. Peaks were collected, and aliquots were assayed for activity.

The amino acid sequence of the purified peptides were determined by standard methods. The purified peptides were reduced and alkylated prior to sequencing by automated Edman degradation on an Applied Biosystems 477A Protein Sequencer with a 120A Analyzer (DNA/Peptide Facility, University of Utah) (Martinez et al., 1995; Shon et al., 1994).

In accordance with this method, peptides AuVA, AuVB and PVA were obtained.

Example 2

Synthesis of conopeptides

The synthesis of conopeptides, either the mature toxins or the precursor peptides, was separately performed using conventional protection chemistry as described by Cartier et al. (1996). Briefly, the linear chains were built on Rink amide resin by Fmoc procedures with 2-(1H-benzotriol-1-yl)-1,1,3,3,-tetramethyluronium tetrafluoroborated coupling using an ABI model 430A peptide synthesizer with amino acid derivatives purchased from Bachem (Torrence, Calif.). Orthogonal protection was used on cysteines: two cysteines were protected as the stable Cys(S-acetamidomethyl), while the other two cysteines were protected as the acid-labile Cys(S-trityl). After removal of the terminal Fmoc protecting group and cleavage of the peptides from the resins, the released peptides were precipitated by filtering the reaction mixture into −10° C. methyl t-butyl ether, which removed the protecting groups except the Cys(S-acetamidomethyl). The peptides were dissolved in 0.1% TFA and 60% acetonitrile and purified by RPLC on a Vydac $C_{18}$ preparative column (22×250 mm) and eluted at a flow rate of 20 mL/min with a gradient of acetonitrile in 0.1% TFA.

The disulfide bridges in the three conopeptides were formed as described in Cartier et al. (1996). Briefly, the disulfide bridges between one pair of cysteines were formed by air oxidation which was judged to be complete by analytical RPLC. The monocyclic peptides were purified by RPLC on a Vydac $C_{18}$ preparative column (22×250 mm) and eluted with a gradient of acetonitrile in 0.1% TFA. Removal of S-acetamidomethyl groups and formation of the disulfide bridge between the other pair of cysteines were carried out simultaneously be iodine oxidation. The cyclic peptides were purified by RPLC on a Vydac $C_{18}$ preparative column (22×250 mm) and eluted with a gradient of acetonitrile in 0.1% TFA.

Example 3

Isolation of DNA Encoding τ-Conotoxins

DNA coding for τ-conotoxins was isolated and cloned in accordance with conventional techniques using general procedures well known in the art, such as described in Olivera et al. (1996). Alternatively, cDNA libraries was prepared from Conus venom duct using conventional techniques. DNA from single clones was amplified by conventional techniques using primers which correspond approximately to the M13 universal priming site and the M13 reverse universal priming site. Clones having a size of approximately 300–500 nucleotides were sequenced and screened for similarity in sequence to known r-conotoxins isolated in Example 1. The DNA sequences and encoded propeptide sequences are set forth in Tables 1–15. DNA sequences coding for the mature toxin can also be prepared on the basis of the DNA sequences set forth in these Tables.

TABLE 1

DNA Sequence (SEQ ID NO:20) and
Protein Sequence (SEQ ID NO:21) of Tx5.1

```
ggtactcaac gaacttcaag acacattctt ttcacctgga cacgggaagc tgactacaag
caga atg tgc tgt ctc cca gtg ttc gtc att ctt ctg ctg att gca
     Met Cys Cys Leu Pro Val Phe Val Ile Leu Leu Leu Leu Ile Ala
tct gca cct agc gtt gat gcc caa ccg aag acc aaa gat gat gtg ccc
Ser Ala Pro Ser Val Asp Ala Gln Pro Lys Thr Lys Asp Asp Val Pro
ctg gca cct ttg cac gat aat gca aag agt gca cta caa cat ttg aac
Leu Ala Pro Leu His Asp Asn Ala Lys Ser Ala Leu Gln His Leu Asn
caa cgc tgc tgc caa aca ttc tat tgg tgc tgt gtt caa ggg aaa
Gln Arg Cys Cys Gln Thr Phe Tyr Trp Cys Cys Val Gln Gly Lys
tgaatttgga tgagacccct gcgaactgtc catggatgtg agatttggaa agcagactgt
tcctttcgca cgtgttcgtg gaattttgaa tggtcgttaa caacacgctg ccacttgcaa
gctactatct ctctgtcctt tcatctgtgg aactggatga cctaacaact gaaatatcat
agaaattttt cagtgggtat acactatgac catgtagtca gtaattacat catttggacc
ttttgaaata tttttcaaaa tgttaagatt tttccccccng gaaaggnctt ttgaagtaaa
tatt
```

TABLE 2

DNA Sequence (SEQ ID NO:22) and
Protein Sequence (SEQ ID NO:23) of G5.1

```
atg tgc tgt ctc cca gtc ttc gtc att ctt ctg ttg ctg att aca tct
Met Cys Cys Leu Pro Val Phe Val Ile Leu Leu Leu Leu Ile Thr Ser
gca cct agc gtt gat gct cta ccg aag acc agg gat gat gtg ccc cta
Ala Pro Ser Val Asp Ala Leu Pro Lys Thr Arg Asp Asp Val Pro Leu
gca tct ttc cac ggt gga tat aat gca agg aga atc cta caa agg cgt
Ala Ser Phe His Gly Gly Tyr Asn Ala Arg Arg Ile Leu Gln Arg Arg
cag ggc tgg tgc tgc aaa gaa aat att gcg tgc tgt ata tagtggtaac
Gln Gly Trp Cys Cys Lys Glu Asn Ile Ala Cys Cys Ile
gggaaatgac tttggatgag acccctgcaa actgtccctg gatgtgaaat ttggaaagta
gactgttcct ttcgcgcgtg ttcgtggaat ttcaaatggt cgtcaacaac acactgctac
ttgcaaagct actatctctc tgtcctttca tctgtggaac tgggtgatct aacagctgaa
atgtcgcaga aattttcaa ttggtctata ctatgaccat gta
```

TABLE 3

DNA Sequence (SEQ ID NO:24) and
Protein Sequence (SEQ ID NO:25) of Qc5.1

```
atg cgc tgt gtc cca gtc ttc atc att ctt ctg ctg ctg agt cca tct
Met Arg Cys Val Pro Val Phe Ile Ile Leu Leu Leu Leu Ser Pro Ser
gca cct agc gtt gat gcc cat ccg atg acc aaa gat gat gtg ccc cag
Ala Pro Ser Val Asp Ala His Pro Met Thr Lys Asp Asp Val Pro Gln
gca tca ttc cat gat gat gca aag cga acc cta caa gta cct tgg atg
Ala Ser Phe His Asp Asp Ala Lys Arg Thr Leu Gln Val Pro Trp Met
aaa cgc ggg tgc tgc gca agg ttg act tgc tgc gtt gga cga
Lys Arg Gly Cys Cys Ala Arg Leu Thr Cys Cys Val Gly Arg
taaagggaaa tgactttgga tgagacccct gcgaactgtc cctggatgtg aaatttggac
agcagactgc tcctttcgca cgtgttcgtg gaattttgaa tggtcgttaa caacacgctg
ccacttgcaa gctattatct ctctgtccct ttatctgtgg aactggataa tctaacaact
gaaatgtcat tgaaattttt caatggatat atattatgat ccatata
```

TABLE 4

DNA Sequence (SEQ ID NO:26) and Protein Sequence (SEQ ID NO:27) of Im5.1

```
aattcggaag ctgactacaa gcaga atg tac tgt ctc cca gtc ttc atc att
                            Met Tyr Cys Leu Pro Val Phe Ile Ile
ctt ctg ctg ctg att tca tct gca cct agc act cct ccc caa cca agg
Leu Leu Leu Leu Ile Ser Ser Ala Pro Ser Thr Pro Pro Gln Pro Arg
aac aaa gat cgt gtg cac ctg ata tct tta ctc gat aat cac aag caa
Asn Lys Asp Arg Val His Leu Ile Ser Leu Leu Asp Asn His Lys Gln
atc cta caa aga gat tgg aac agt tgc tgt ggg aaa aat cct ggt tgc
Ile Leu Gln Arg Asp Trp Asn Ser Cys Cys Gly Lys Asn Pro Gly Cys
tgt cct tgg gga aaa tgactttgga tgagacccct gcaaactgtc cctggatgtg
Cys Pro Trp Gly Lys
agatttggaa agcagaccgt tgtggaatt ttgaatggtc gttaacaaca cgctgccact
tgcaagctac aatctctctg tcctttcatc tttggaactg gatgatcaaa caactgaaat
gtcatagaaa tttttcaatg ggtatacaat atgtgggcat ttagtcagta attacatcat
ttgg
```

TABLE 5

DNA Sequence (SEQ ID NO:28) and Protein Sequence (SEQ ID NO:29) of G5.2

```
atg tgc tgt ctc cca gtc ttc gtc att ctt ctg ttg ctg att aca tct
Met Cys Cys Leu Pro Val Phe Val Ile Leu Leu Leu Leu Ile Thr Ser
gca cct agc gtt gat gct cta ccg aag acc agg gat gat gtg ccc cta
Ala Pro Ser Val Asp Ala Leu Pro Lys Thr Arg Asp Asp Val Pro Leu
gca tct ttc cac ggt gga tat aat gca agg aga atc cta caa agg cgt
Ala Ser Phe His Gly Gly Tyr Asn Ala Arg Arg Ile Leu Gln Arg Arg
cag ggc tgg tgc tgc aaa gaa aat att gcg tgc tgt gta tagtggtaac
Gln Gly Trp Cys Cys Lys Glu Asn Ile Ala Cys Cys Val
gggaaatgac tttggatgag acccctgcaa actgtcctg gatgtgaaat tggaaagta
gactgttcct ttcgcgcgtg ttcgtggaat ttcaaatggt cgtcaacaac acactgctac
ttgcaaagct actatctctc tgtcctttca tctgtggaac tgggtgatct aacagctgaa
atgtcgcaga aattttttcaa ttggtctata ctatgaccat gtagtcag
```

TABLE 6

DNA Sequence (SEQ ID NO:30) and Protein Sequence (SEQ ID NO:31) of Tx5.2a

```
atg cgc tgt ttc cca gtc ttc atc att ctt ctg ctg cta att gca tct
Met Arg Cys Phe Pro Val Phe Ile Ile Leu Leu Leu Leu Ile Ala Ser
gca cct tgc ttt gat gcc cga acg aag acc gat gat gat gtg ccc ctg
Ala Pro Cys Phe Asp Ala Arg Thr Lys Thr Asp Asp Asp Val Pro Leu
tca tct ctc cgc gat aat cta aag cga acg ata cga aca cgc ctg aac
Ser Ser Leu Arg Asp Asn Leu Lys Arg Thr Ile Arg Thr Arg Leu Asn
ata cgc gag tgc tgc gag gat gga tgg tgc tgt act gct gca ccc tta
Ile Arg Glu Cys Cys Glu Asp Gly Trp Cys Cys Thr Ala Ala Pro Leu
aca ggt cgt tagggataaa ggaaaatggc tttggatgag acccctgcga
Thr Gly Arg
attgtccctg gatgtgagat ttggaaagca gactgttcct ttcgcacgtg ttcgtggaat
ttcgaatggt cgttaacaac acgctgccac tgcaagcca ccatctctct gtcctttcgt
atgtggaact gtatgatcta caactgaaa tgtcagaaag ttttcagtgg gtatacacta
tgatcgtata
```

TABLE 7

DNA Sequence (SEQ ID NO:32) and Protein Sequence (SEQ ID NO:33) of Tx5.2b

```
atg cgc tgt ttc cca gtc ttc atc att ctt ctg ttg cta att gca tct
Met Arg Cys Phe Pro Val Phe Ile Ile Leu Leu Leu Leu Ile Ala Ser
gca cct tgc ttt gat gcc cga acg aag acc gat gat gat gtg ccc ctg
Ala Pro Cys Phe Asp Ala Arg Thr Lys Thr Asp Asp Asp Val Pro Leu
tca tct ctc cgc gat aat cta aag cga acg ata cga aca cgc ctg aac
Ser Ser Leu Arg Asp Asn Leu Lys Arg Thr Ile Arg Thr Arg Leu Asn
ata cgc ggg tgc tgc gag gat gga tgg tgc tgt act gct gca ccc tta
Ile Arg Gly Cys Cys Glu Asp Gly Trp Cys Cys Thr Ala Ala Pro Leu
aca ggt cgt tagggataaa ggaaaatggc tttggatgag acccctgcaa
Thr Gly Arg
attgtccctg gatgtgagat ttggaaagca gactgttcct ttcgcacgtg ttcgtggaat
```

TABLE 7-continued

DNA Sequence (SEQ ID NO:32) and
Protein Sequence (SEQ ID NO:33) of Tx5.2b ttcgaatggt cgttaacaac acgctgccac ttgcaagcca ccatctctct gtcctttcgt
atgtggaact gtatgatcta acaactgaaa tgtcagaaag ttttcagtgg gtatacacta
tgatcgtata gtcagtaatt

TABLE 8

DNA Sequence (SEQ ID NO:34) and
Protein Sequence (SEQ ID NO:35) of Mr5.1 atg cgc tgc ctc cca gtc ttc gtc att ctt ctg ctg ctg att gca tct
Met Arg Cys Leu Pro Val Phe Val Ile Leu Leu Leu Leu Ile Ala Ser
gca cct agc gtt gat gcc cga ccg aag acc aaa gat gat atg ccc ctg
Ala Pro Ser Val Asp Ala Arg Pro Lys Thr Lys Asp Asp Met Pro Leu
gca tct ttc cat gat aat gca aag cga atc ctg caa ata ctt cag gac
Ala Ser Phe His Asp Asn Ala Lys Arg Ile Leu Gln Ile Leu Gln Asp
aga aat ggt tgc tgc aga gca gga gac tgc tgt tca cga ttt gag ata
Arg Asn Gly Cys Cys Arg Ala Gly Asp Cys Cys Ser Arg Phe Glu Ile
aag gaa aat gac ttt gga tgagacccct gcaaactgtc cttggatgtg
Lys Glu Asn Asp Phe Gly
agatttggaa agcagactgt tcctttcgca cgtgttcgtg gaatttcgaa tggtcgttaa
caacacgctg ccacttgcaa gctactatct ctctgtcctt tgtctgtgg aactgtatga
tcaaacaact gaaatgtcat agaaatttt cagtgggtaa acactatgac catgta

TABLE 9

DNA Sequence (SEQ ID NO:36) and
Protein Sequence (SEQ ID NO:37) of Mr5.2 ga atg cgc tgc ctc cca gtc ttc gtc att ctt ctg ctg ctg att gca
   Met Arg Cys Leu Pro Val Phe Val Ile Leu Leu Leu Leu Ile Ala
tct gca cct agc gtt gat gcc cga ccg aag acc aaa gat gat atg ccc
Ser Ala Pro Ser Val Asp Ala Arg Pro Lys Thr Lys Asp Asp Met Pro
ctg gca tct ttc cac gat aat gca aag cga atc ctg caa ata ctt cag
Leu Ala Ser Phe His Asp Asn Ala Lys Arg Ile Leu Gln Ile Leu Gln
gac aga aat gct tgc tgc ata gta agg cag tgc tgt tgatgatttg
Asp Arg Asn Ala Cys Cys Ile Val Arg Gln Cys Cys
agataaagga aaatgacttt ggatgagacc cctgcaaact gtccctggat gtgagatttg
gaaagcagac tgttcctttc gcacgtgttc gtggaatttc gaatggtcgt taacaacacg
ctgccacttg caagctacta tctctctgtc ctttcatctg tggaactgta tgatcaaaca
actgaaatgt catagaaatt tttcagtggg taaacactat gatcatgtag tcagtaatta
catcatttgg aattccatca agcttatcga taccgtcgac ctcgaggggg ggcccggt

TABLE 10

DNA Sequence (SEQ ID NO:38) and
Protein Sequence (SEQ ID NO:39) of Mr5.3 atg cgc tgc ctc cca gtc ttt gtc att ctt ctg ctg ctg att gca tct
Met Arg Cys Leu Pro Val Phe Val Ile Leu Leu Leu Leu Ile Ala Ser
gca cct agc gtt gat gcc cga ccg aag acc aaa gat gat atg ccc ctg
Ala Pro Ser Val Asp Ala Arg Pro Lys Thr Lys Asp Asp Met Pro Leu
gca tct ttc cat gat aat gca aag cga atc ctg caa ata ctt cag gac
Ala Ser Phe His Asp Asn Ala Lys Arg Ile Leu Gln Ile Leu Gln Asp
aga aat ggt tgc tgc aga gca gga gac tgc tgt tca tgatttgaga
Arg Asn Gly Cys Cys Arg Ala Gly Asp Cys Cys Ser
taaagggaaa tgactttgga tgagacccct gcaaactgtc cttggatgtg agatttggaa
agcagactgt tcctttcgca cgtgttcgtg gaatttcgaa tggtcgttaa caacacgctg
ccacttgcaa gctactatct ctctgtcctt tcatctgtgg aactgtatga tcaaacaact

TABLE 11

DNA Sequence (SEQ ID NO:40) and
Protein Sequence (SEQ ID NO:41) of Ca5.1 atg cgc tgt ctc ccg gtc ttc atc att ctt ctg ctg ctg att gca tct
Met Arg Cys Leu Pro Val Phe Ile Ile Leu Leu Leu Leu Ile Ala Ser
gca cct ggc gtt gat gcc caa ccg aag acc aaa tat aat gcg ccc ctg
Ala Pro Gly Val Asp Ala Gln Pro Lys Thr Lys Tyr Asn Ala Pro Leu TABLE 11-continued DNA Sequence (SEQ ID NO:40) and
Protein Sequence (SEQ ID NO:41) of Ca5.1

```
aca tct ctc cac gat aat gca aag ggt ata cta caa gaa cat tgg aac
Thr Ser Leu His Asp Asn Ala Lys Gly Ile Leu Gln Glu His Trp Asn
aaa cgc tgc tgc ccc aga agg ctt gcc tgc tgt att ata gga cgg aaa
Lys Arg Cys Cys Pro Arg Arg Leu Ala Cys Cys Ile Ile Gly Arg Lys
tggatgattt tgggtgagat ccctgcaaac tgtccctgga tttgaatttt ggaaagcaga
ctgttccttt cgcacgtgtt cgtggaattt cgaatggtcg ttaacaacac gctgccactt
gcaagctact atctctctgt ccttttctc tgtgaaactg gatggtctaa caactgaaat
gtcatagaaa attttcaatg ggtatactct atgaccatct a
```

TABLE 12

DNA Sequence (SEQ ID NO:42) and
Protein Sequence (SEQ ID NO:43) of Ca5.2

```
atg cgc tgt ctc cca gtc ttc atc att ctt ctg ctg ctg att gca tct
Met Arg Cys Leu Pro Val Phe Ile Ile Leu Leu Leu Leu Ile Ala Ser
gca cct ggc gtt gat gcc caa ccg aag acc aaa tat gat gcg ccc ctg
Ala Pro Gly Val Asp Ala Gln Pro Lys Thr Lys Tyr Asp Ala Pro Leu
aca tct ctc cac gat aat gca aag ggt ata cta caa gaa cat tgg aac
Thr Ser Leu His Asp Asn Ala Lys Gly Ile Leu Gln Glu His Trp Asn
aaa cgc tgc tgc ccc aac aag cct tgc tgt ttt ata gga agg aaa
Lys Arg Cys Cys Pro Asn Lys Pro Cys Cys Phe Ile Gly Arg Lys
tgaatgattt tgggtgagac ccctgcaaac tgtccctgga tttgaatttt ggaaagcaga
ctgttcctt cgcacgtgtt cgtggaattt cgaatggtcg ttaacaacac gctgccactt
gcaagctact atctctctgt ccttttctc tgtgaaactg gatggtctaa caactgagat
gtcatagaaa attttcaatc ggtgtactct atgaccatct a
```

TABLE 13

DNA Sequence (SEQ ID NO:44) and
Protein Sequence (SEQ ID NO:45) of Qc5.2

```
atg cgc tgt gtc cca gtc ttc atc att ctt ctg ctg ctg agt cca tct
Met Arg Cys Val Pro Val Phe Ile Ile Leu Leu Leu Leu Ser Pro Ser
gca cct agc gtt gat gcc cat ccg atg acc aaa gat gat gta ccc cag
Ala Pro Ser Val Asp Ala His Pro Met Thr Lys Asp Asp Val Pro Gln
gca tct ctc cat gat gat gca aag cga acc cta caa gta cct tgg atg
Ala Ser Leu His Asp Asp Ala Lys Arg Thr Leu Gln Val Pro Trp Met
aaa cgc ggg tgc tgc gca atg ttg act tgc tgc gtt gga cga
Lys Arg Gly Cys Cys Ala Met Leu Thr Cys Cys Val Gly Arg
taaagggaaa tgactttgga tgagacccct acgaactgtc cctggatgtg aaatttggac
agcagactgc tcctttcgca cgtgttcgtg gaatttcgaa tggtcgttaa caacacgctg
ccacttgcaa gctattatct ctctgtccct ttatctgtgg aactggataa tctaacaact
gaaacgtcat tgaaaatttt caatggatat atattatgat ccatata
```

TABLE 14

DNA Sequence (SEQ ID NO:46) and
Protein Sequence (SEQ ID NO:47) of Gm5.1

```
gggcaggtac tcaacgaact tcaggacaca ttcttttcac ctggacacgg gaaactgact
ataagcaga atg cgc tac cta cca gtc ttc gtc att ctt ctg ctg ctg att
          Met Arg Tyr Leu Pro Val Phe Val Ile Leu Leu Leu Leu Ile
gca tct ata cct agc gat act gtc caa ctg aag acc aaa gat gat atg
Ala Ser Ile Pro Ser Asp Thr Val Gln Leu Lys Thr Lys Asp Asp Met
ccc ctg gca tct ttc cac ggt aat gga aga cga atc ctg cga atg ctt
Pro Leu Ala Ser Phe His Gly Asn Gly Arg Arg Ile Leu Arg Met Leu
tca aac aaa cgc tta tgc tgt gtc acc gag gat tgg tgc tgt gaa tgg
Ser Asn Lys Arg Leu Cys Cys Val Thr Glu Asp Trp Cys Cys Glu Trp
tgg taaaggaaaa tgactttgga tgagacccct gcaaactgtt tctggatgtg
Trp
agatttggaa agcagactgt tctttcgcac gtattcgtga aatttcgaat ggtcgttaac
aacacgctgc cacttgcaag ctgctatctc tctgtctttt catctgtgga actgtatgat
ctaacaactg aaatgtcata gacattttc attgggtata cactgtgacc atgtagccag
taattacatc atttggacct tttggatatt tcagtatg taagtgtgtt ccccttaaaaa
gtcctttgta attatgtatt ttaanaattt angttttgca cataaattgt aaaacgctgt
cctttctgtt gntcctacat cantggtggg gaaaagnaaa atgtttggcc ntggtcaaat
ttaaataatn accctgccgt ttnaatgcng ttattantgg tattttnaac nttgnacggt
taaactt
```

TABLE 15

DNA Sequence (SEQ ID NO:48) and
Protein Sequence (SEQ ID NO:49) of Gm5.2

```
ga atg cgc tgt ctc cca gtc ttc gtc att ctt ctg ctg ctg att gca
   Met Arg Cys Leu Pro Val Phe Val Ile Leu Leu Leu Leu Ile Ala
tct gca cct agc gtt gat gcc caa ccg aag acc aaa gat gat gtg ccc
Ser Ala Pro Ser Val Asp Ala Gln Pro Lys Thr Lys Asp Asp Val Pro
ctg gca cct ttg cac gat aat ata agg agt act cta caa aca ctt cgg
Leu Ala Pro Leu His Asp Asn Ile Arg Ser Thr Leu Gln Thr Leu Arg
aag aaa gtc tgc tgc cgc cca gtg cag gat tgc tgt tca ggg aaa
Lys Lys Val Cys Cys Arg Pro Val Gln Asp Cys Cys Ser Gly Lys
tgaagggaaa tgaatttgga tgagacccct gcgaactgtc cctggatgtg agatttggaa
agcagactgt tcctttcgca cgtgttcgtg gaatttcgaa tggtcgttaa caacacgctg
ccacttgcaa gctactatct ctctgtcctt tcatctgcgg aactggatga cctaaagctt
gtgatc
```

Example 4

Biological Activity of τ-Conotoxins

The biological activity of τ-conotoxin peptides at the acetylcholine receptor was tested in the fluorescence assay as described by Cornell-Bell et al. (1999). Briefly, primary cortical cells are exposed to acetylcholine in the presence or absence of a τ-conotoxin peptide. Acetylcholine causes the primary cortical cells to flux calcium, which is measured by increases in fluorescence in cells loaded with Fluo-3, a calcium imaging dye. The τ-conotoxin peptide AuVA inhibited the response of primary cortical cells to acetylcholine at low concentrations (10 pM) at 15 seconds following exposure to the peptide and acetylcholine. This study shows that the τ-conotoxin peptide acts at the acetylcholine receptor.

Example 5

Effect of τ-Conotoxins in a Pain Model

The effect of τ-conotoxin peptides for use in treating pain was by testing in two pain models, the first being the hind-paw licking model (Woolfe and MacDonald, 1944; Plummer et al., 1991; Suh et al., 1992; Plone et al., 1996) and the second being the accelerating roto-rod model. In the hind-paw licking model, it was found that 10 nmol of τ-conotoxin peptide AuVA increased the latency to initiate hind-paw licking in mice on a 55° C. hot plate 15 minutes following freehand intracerebroventricular (i.c.v.) injection. It was further found that 1 nmol τ-conotoxin peptide AuVA did not have any effect in this model. In the accelerating roto-rod model, it was found that τ-conotoxin peptide AuVA produced impairment of motor performance following injection of τ-conotoxin peptide AuVA. The effects seen in these models demonstrates that the τ-conotoxin peptides have analgesic properties.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Barnay, G. et al. (2000). *J. Med. Chem.*
Bitan, G. et al. (1997). *J. Peptide Res.* 49:421–426.
Bodansky et al. (1966). *Chem. Ind.* 38:1597–98.
Cartier, G. E. et al. (1996). *J. Biol. Chem.* 271:7522–7528.
Cornell-Bell, A. H. et al. (1999). Kainate spiral waves and integrins: A signaling system without gap junctions. *Glia*, in press.
Cruz, L. J. et al. (1976). *Verliger* 18:302–308.
Cruz, L. J. et al. (1987). *J. Biol. Chem.* 260:9280–9288.
Haack, J. A. et al. (1990). *J. Biol. Chem.* 265:6025–6029.
Hammerland et al. (1 992). *Eur. J. Pharmacol.* 226:239–244.
Horiki, K. et al. (1 978). *Chemistry Letters* 165–68.
Hubry, V. et al. (1994). *Reactive Polymers* 22:231–241.
Kapoor (1970). *J. Pharm. Sci.* 59:1–27.
Kornreich, W. D. et al. (1986). U.S. Pat. No. 4,569,967.
Martinez, J. S. et al. (1995). *Biochem.* 34:14519–14526.
McIntosh, J. M. et al. (1982). *Arch. Biochem. Biophys.* 218:329–334.
Mena, E. E. et al. (1990). *Neurosci. Lett.* 118:241–244.
*Methoden der Organischen Chemie (Houben-Weyl): Synthese von Peptiden*, E. Wunsch (Ed.), Georg Thieme Verlag, Stuttgart, Ger. (1974).
Myers, R. A. et al. (1991). *Biochemistry* 30:9370–9377.
Nishiuchi, Y. et al. (1993). *Int. J. Pept. Protein Res.* 42:533–538.
Nowak, L. et al. (1984). *Nature* 307:462–465.
Olivera, B. M. et al. (1984). U.S. Pat. No. 4,447,356.
Olivera, B. M. et al. (1985). *Science* 230:1338–1343.
Olivera, B. M. et al. (1996). U.S. Pat. No. 5,514,774.
Ornstein, et al. (1993). *Biorganic Medicinal Chemistry Letters* 3:43–48.
Plone, M. A. et al. (1996). *Pain* 66:265–70.
Plummer, J. L. et al. (1991). *J Pharmacol Methods* 26:79–87.
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual*, 2nd Ed., Cold Spring Harbor Laboratory, Cold Spring Harbor, N.Y.
Schroder & Lubke (1965). *The Peptides* 1:72–75, Academic Press, NY.
Shon, K.-J. et al. (1994). *Biochemistry* 33:11420–11425.
Stewart and Young, *Solid-Phase Peptide Synthesis*, Freeman & Co., San Francisco, Calif. (1969).
Suh, H. H. et al. (1992). *Eur J Pharmacol* 213:337–41.
Vale et al. (1978). U.S. Pat. No. 4,105,603.
Van de Steen, P. et al. (1998). *Critical Rev. in Biochem. and Mol. Biol.* 33:151–208.

Woolfe, G. and MacDonald, A. (1944). *J. Pharmacol. Exp. Ther.* 80:300–307.

Zafaralla, G. C. et al. (1988). *Biochemistry* 27:7102–7105.

Zhou L. M., et al. (1996). *J. Neurochem.* 66:620–628.

U.S. Pat. No. 3,972,859.
U.S. Pat. No. 3,842,067.
U.S. Pat. No. 3,862,925.
U.S. Pat. No. 5,514,774.
U.S. Pat. No. 5,531,001.
U.S. Pat. No. 5,534,615.
U.S. Pat. No. 5,364,769.
U.S. Pat. No. 5,545,723.
U.S. Pat. No. 5,550,050.
U.S. Pat. No. 5,591,821.
U.S. Pat. No. 5,719,264.
U.S. Pat. No. 5,844,077.
PCT Published Application WO 92/19195.
PCT Published Application WO 94/25503.
PCT Published Application WO 95/01203.
PCT Published Application WO 95/05452.
PCT Published Application WO 96/02286.
PCT Published Application WO 96/02646.
PCT Published Application WO 96/11698.
PCT Published Application WO 96/40871.
PCT Published Application WO 96/40959.
PCT Published Application WO 97/12635.
PCT Published Application WO 98/03189.

What is claimed is:

1. A substantially pure τ-conotoxin peptide having the generic formula I: Xaa$_1$-Xaa$_2$-Xaa$_3$-Xaa$_4$-Cys-Cys-Xaa$_5$-Xaa$_6$-Xaa$_7$-Xaa$_8$-Xaa$_9$-Cys-Cys-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Xaa$_{18}$-Xaa$_{19}$ (SEQ ID NO:1), wherein Xaa$_1$ is des-Xaa$_1$, Asp, Glu or γ-carboxy-Glu(Gla); Xaa$_2$ is des-Xaa$_2$, Gln, Asn, Glu, Trp (D or L), neo-Trp, halo-Trp or any unnatural aromatic amino acid; Xaa$_3$ is des-Xaa$_3$, Gly, Ala, Asn or Gln; Xaa$_4$ is des-Xaa$_4$, Val, Leu (D or L), Ile, Ala, Gly, Glu, Gla, Asp, Ser, Thr, Phe, Trp (D or L), neo-Trp, halo-Trp (D or L) or any unnatural aromatic amino acid; Xaa$_5$ is Pro, hydroxy-Pro, Gln, Asn, Glu, Gla, Ala, Gly, Lys, Arg, Ile, Val, homoarginine, ornithine, N-methyl-Lys, N,N-dimethyl-Lys, N,N,N-trimethyl-Lys or any unnatural basic amino acid; Xaa$_6$ is Val, Phe, Thr, Ser, Glu, Gla, Asp, Asn, Gln, Ala, Gly, Ile, Leu (D or L), Met, Pro, hydroxy-Pro, Arg, homoarginine, ornithine, Lys, N-methyl-Lys, N,N-dimethyl-Lys, N,N,N-trimethyl-Lys, any unnatural basic amino acid or any unnatural aromatic amino acid; Xaa$_7$ is any Val, Ile, Asn, Leu (D or L), Gln, Gly, Ala, Phe, Glu, Gla, Arg, ornithine, homoarginine, Lys, N-methy-Lys, N,N-dimethyl-Lys, N,N,N-trimethyl-Lys, any unnatural basic amino acid or any unnatural aromatic amino acid; $Xaa_8$ is Ile, Leu (D or L), Met, Thr, Ser, Pro, hydroxy-Pro, Gln, Asp, Glu, Gla, Asn, Arg, homoarginine, ornithine, Lys, N-methy-Lys, N,N-dimethyl-Lys, N,N,N-trimethyl-Lys, Tyr, nor-Tyr, mono-halo-Tyr, di-halo-Tyr, O-sulpho-Tyr, O-phospho-Tyr, nitro-Tyr, any unnatural basic amino acid, any unnatural aromatic amino acid or any unnatural hydroxy containing amino acid; $Xaa_9$ is des-$Xaa_9$, Ala, Gly, Asp, Glu, Gla, Trp (D or L) neo-Trp, halo-Trp (D or L), Lys, N-methy-Lys, N,N-dimethyl-Lys, N,N,N-trimethyl-Lys, Arg, homoarginine, ornithine, Tyr, nor-Tyr, mono-halo-Tyr, di-halo-Tyr, O-sulpho-Tyr, O-phospho-Tyr, nitro-Tyr or any unnatural basic amino acid; $Xaa_{10}$ is des-$Xaa_{10}$, Ile, Leu (D or L), Val, Glu, Gla, Asp, Thr, Ser, Pro, hydroxy-Pro, Trp (D or L), neo-Trp, halo-Trp (D or L), Phe, any unnatural aromatic amino acid or any unnatural hydroxy containing amino acid; $Xaa_{11}$ is des-$Xaa_{11}$, Gln, Asn, Leu (D or L), Ile, Val, Ala, Gly, Trp (D or L), neo-Trp, halo-Trp (D or L), Arg, homoarginine, ornithine, Lys, N-methy-Lys, N,N-dimethyl-Lys, N,N,N-trimethyl-Lys, any unnatural basic amino acid or any unnatural aromatic amino acid; $Xaa_{12}$ is des-$Xaa_{12}$, Ala, Gly, Phe, Trp (D or L), neo-Trp, halo-Trp (D or L) or any unnatural aromatic amino acid; $Xaa_{13}$ is des-$Xaa_{13}$, Glu, Gla, Asp, Phe or any unnatural aromatic amino acid; $Xaa_{14}$ is des-$Xaa_{14}$, Ile, Val or Leu (D or L); $Xaa_{15}$ is des-$Xaa_{15}$, Thr, Ser, Arg, homoarginine, ornithine, Lys, N-methy-Lys, N,N-dimethyl-Lys, N,N,N-trimethyl-Lys or any unnatural basic amino acid; $Xaa_{16}$ is des-$Xaa_{16}$, Glu, Gla or Asp; $Xaa_{17}$ is des-$Xaa_{17}$, Asn or Gln; $Xaa_{18}$ is des-$Xaa_{18}$, Asp, Glu or Gla; $Xaa_{19}$ is des-$Xaa_{19}$, Phe or any unnatural aromatic amino acid; and the C-terminus contains a free carboxyl group or an amide group.

2. The substantially pure α-conotoxin peptide of claim 1, which is modified to contain an O-glycan, an S-glycan or an N-glycan.

3. A substantially pure τ-conotoxin peptide consisting of
Phe-Cys-Cys-$Xaa_1$-Phe-Ile-Arg-$Xaa_2$-Cys-Cys-$Xaa_3$ (SEQ ID NO:3);
wherein $Xaa_1$ is Pro or hydroxy-Pro; $Xaa_2$ is Tyr, mono-halo-Tyr, di-halo-Tyr, O-sulpho-Tyr, O-phospho-Tyr or nitro-Tyr; $Xaa_3$ is Trp or halo-Trp; and the C-terminus contains a carboxyl or amide group.

4. The substantially pure τ-conotoxin peptide of claim 3, wherein $Xaa_2$ is Tyr.

5. The substantially pure τ-conotoxin peptide of claim 2, wherein $Xaa_3$ is Trp.

6. The substantially pure τ-conotoxin peptide of claim 2, wherein $Xaa_1$ is Pro or hydroxy-Pro, $Xaa_2$ is Tyr, mono-iodo-Tyr or di-iodo-Tyr, and $Xaa_3$ is Trp.

7. The substantially pure τ-conotoxin peptide of claim 2, wherein $Xaa_1$ is Pro, $Xaa_2$ is Tyr and $Xaa_3$ is Trp.

8. The substantially pure τ-conotoxin peptide of claim 2 which is modified to contain an O-glycan, an S-glycan or an N-glycan.

* * * * *

SEQUENCE LISTING

<160> NUMBER OF SEQ ID NOS: 49

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence:Generic
      Sequence for Tau Conopeptides
<220> FEATURE:
<221> NAME/KEY: PEPTIDE
<222> LOCATION: (1)..(2)
<223> OTHER INFORMATION: Xaa at residue 1 is Asp, Glu or
      gamma-carboxy-Glu (Gla); Xaa at residue 2 is des-Xaa, Gln, Asn,
      Glu, Trp (D or L), neo-Trp, halo-Trp, any unnatural aromatic amino
      acid.
<220> FEATURE:
<221> NAME/KEY: PEPTIDE
<222> LOCATION: (3)..(4)
<223> OTHER INFORMATION: Xaa at residue 3 is des-Xaa, Gly, Ala, Asn or
      Gln; Xaa at residue 4 is des-Xaa4,Val, Leu (D or L), Ile, Ala,
      Gly, Glu, Gla, Asp, Ser, Thr, Phe, Trp (D or L), neo-Trp, halo-Trp
      (D or L) or any
<220> FEATURE:
<221> NAME/KEY: PEPTIDE
<222> LOCATION: (4)..(7)
<223> OTHER INFORMATION: unnatural aromatic amino acid; Xaa at residue 7
      is Pro, hydroxy-Pro, Gln, Asn, Glu, Gla, Ala, Gly, Lys, Arg, Ile,
      Val, homoarginine, ornithine, N-methyl-Lys, N,N-dimethyl-Lys,
      N,N,N-trimethyl-Lys or
<220> FEATURE:
<221> NAME/KEY: PEPTIDE
<222> LOCATION: (7)..(8)
<223> OTHER INFORMATION: any unnatural basic amino acid; Xaa at residue
      8 is Val, Phe, Thr, Ser, Glu, Gla, Asp, Asn, Gln, Ala, Gly, Ile,
      Leu (D or L), Met, Pro, hydroxy-Pro, Arg, homoarginine, ornithine,
      Lys, N-methyl-Lys,
<220> FEATURE:
<221> NAME/KEY: PEPTIDE
<222> LOCATION: (8)..(9)
<223> OTHER INFORMATION: N,N,-dimethyl-Lys, N,N,N-trimethyl-Lys, any
      unnatural basic amino acid or any unnatural
      aromatic amino acid; Xaa at residue 9 is Val, Ile,
      Asn, Leu (D or L), Gln, Gly, Ala, Phe, Glu, Gla,
      Arg,
<220> FEATURE:
<221> NAME/KEY: PEPTIDE
<222> LOCATION: (9)..(10)
<223> OTHER INFORMATION: ornithine, arginine, Lys, N-methy-Lys,
      N,N-dimethyl-Lys, N,N,N-trimethyl-Lys, any
      unnatural basic amino acid or any unnatural
      aromatic amino acid; Xaa at residue 10 is Ile, Leu
      (D or L), Met, Thr,
<220> FEATURE:
<221> NAME/KEY: PEPTIDE

```
<222> LOCATION: (10)
<223> OTHER INFORMATION: Ser, Pro, hydroxy-Pro, Gln, Asp, Glu, Gla, Asn,
      Arg, homoarginine, ornithine, Lys, N-methy-Lys,
      N,N-dimethyl-Lys, N,N,N-trimethyl-Lys, Tyr,
      nor-Tyr, mono-halo-Tyr, di-halo-Tyr, O-sulpho-Tyr,
<220> FEATURE:
<221> NAME/KEY: PEPTIDE
<222> LOCATION: (10)..(11)
<223> OTHER INFORMATION: O-phosopho-Tyr, nitro-Tyr, any unnatural basic
      amino acid, any unnatural aromatic amino acid or
      any unnatural hydroxy containing amino acid; Xaa
      at residue 11 is des-Xaa, Ala, Gly, Asp, Glu, Gla,
<220> FEATURE:
<221> NAME/KEY: PEPTIDE
<222> LOCATION: (11)
<223> OTHER INFORMATION: Trp (D or L), neo-Trp, halo-Trp (D or L), Lys,
      N-methy-Lys, N,N-dimethyl-Lys,
      N,N,N-trimethyl-Lys, Arg, homoarginine, ornithine,
      Tyr, nor-Tyr, mono-halo-Tyr, di-halo-Tyr,
      O-sulpho-Tyr, O-phospho-Tyr,
<220> FEATURE:
<221> NAME/KEY: PEPTIDE
<222> LOCATION: (11)..(14)
<223> OTHER INFORMATION: nitro-Tyr or any unnatural basic amino acid;
      Xaa at residue 14 is des-Xaa, Ile, Leu (D or L), Val, Glu, Gla,
      Asp, Thr, Ser, Pro, hydroxy-Pro, Trp (D or L), neo-Trp, halo-Trp
      (D or L), Phe, any
<220> FEATURE:
<221> NAME/KEY: PEPTIDE
<222> LOCATION: (14)..(15)
<223> OTHER INFORMATION: unnatural aromatic amino acid or any unnatural
      hydroxy containing amino acid; Xaa at residue 15
      is des-Xaa11, Gln, Asn, Leu (D or L), Ile, Val,
      Ala, Gly, Trp (D or L), neo-Trp, halo-Trp (D or
      L), Arg,
<220> FEATURE:
<221> NAME/KEY: PEPTIDE
<222> LOCATION: (15)..(16)
<223> OTHER INFORMATION: homoarginine, ornithine, Lys, N-methy-Lys,
      N,N-dimethyl-Lys, N,N,N-trimethyl-Lys, any
      unnatural basic amino acid or any unnatural
      aromatic amino acid; Xaa at residue 16 is des-Xaa,
      Ala, Gly, Phe,
<220> FEATURE:
<221> NAME/KEY: PEPTIDE
<222> LOCATION: (16)..(17)
<223> OTHER INFORMATION: Trp (D or L), neo-Trp, halo-Trp (D or L) or any
      unnatural aromatic amino acid; Xaa at residue 17
      is des-Xaa, Glu, Gla, Asp, Phe or any unnatural
      aromatic amino acid.
<220> FEATURE:
<221> NAME/KEY: PEPTIDE
<222> LOCATION: (18)..(19)
<223> OTHER INFORMATION: Xaa at residue 18 is des-Xaa, Ile, Val or Leu
      (D or L); Xaa at residue 19 is des-Xaa, Thr, Ser, Arg,
      homoarginine, ornithine, Lys, N-methy-Lys, N,N-dimethyl-Lys,
      N,N,N-trimethyl-Lys or any unnatural
<220> FEATURE:
<221> NAME/KEY: PEPTIDE
<222> LOCATION: (19)..(22)
<223> OTHER INFORMATION: basic amino acid; Xaa at residue 20 is des-Xaa,
      Glu, Gla or Asp; Xaa at residue 21 is des-Xaa, Asn
      or Gln; Xaa at residue 22 is des-Xaa, Asp, Glu or
      Gla.
<220> FEATURE:
<221> NAME/KEY: PEPTIDE
<222> LOCATION: (23)
<223> OTHER INFORMATION: Xaa at residue 23 is des-Xaa, Phe or any
      unnatural aromatic amino acid.

<400> SEQUENCE: 1

Xaa Xaa Xaa Xaa Cys Cys Xaa Xaa Xaa Xaa Xaa Cys Cys Xaa Xaa Xaa
 1               5                  10                  15

Xaa Xaa Xaa Xaa Xaa Xaa Xaa
            20
```

```
<210> SEQ ID NO 2
<211> LENGTH: 11
<212> TYPE: PRT
<213> ORGANISM: Conus aulicus
<220> FEATURE:
<221> NAME/KEY: PEPTIDE
<222> LOCATION: (4)..(8)
<223> OTHER INFORMATION: Xaa at residue 4 is Pro or hydroxy-Pro; Xaa at
      residue 8 is Tyr, nor-Tyr, mono-halo-Tyr, di-halo-Tyr,
      O-sulpho-Tyr, O-phospho-Tyr or nitro-Tyr.
<220> FEATURE:
<221> NAME/KEY: PEPTIDE
<222> LOCATION: (11)
<223> OTHER INFORMATION: Xaa at residue 11 is Trp (D or L), neo-Trp or
      halo-Trp (D or L).

<400> SEQUENCE: 2

Phe Cys Cys Xaa Val Ile Arg Xaa Cys Cys Xaa
  1               5                  10

<210> SEQ ID NO 3
<211> LENGTH: 11
<212> TYPE: PRT
<213> ORGANISM: Conus aulicus
<220> FEATURE:
<221> NAME/KEY: PEPTIDE
<222> LOCATION: (4)..(8)
<223> OTHER INFORMATION: Xaa at residue 4 is Pro or hydroxy-Pro; Xaa at
      residue 8 is Tyr, nor-Tyr, mono-halo-Tyr,
      di-halo-Tyr, O-sulpho-Tyr, O-phospho-Tyr or
      nitro-Tyr.
<220> FEATURE:
<221> NAME/KEY: PEPTIDE
<222> LOCATION: (11)
<223> OTHER INFORMATION: Xaa at residue 11 is Trp (D or L), neo-Trp or
      halo-Trp (D or L).

<400> SEQUENCE: 3

Phe Cys Cys Xaa Phe Ile Arg Xaa Cys Cys Xaa
  1               5                  10

<210> SEQ ID NO 4
<211> LENGTH: 10
<212> TYPE: PRT
<213> ORGANISM: Conus textile
<220> FEATURE:
<221> NAME/KEY: PEPTIDE
<222> LOCATION: (6)..(7)
<223> OTHER INFORMATION: Xaa at residue 6 is Tyr, mono-halo-Tyr,
      di-halo-Tyr, O-sulpho-Tyr, O-phospho-Tyr or nitro-Tyr; Xaa at
      residue 7 is Trp (D or L), neo-Trp or halo-Trp (D or L).

<400> SEQUENCE: 4

Cys Cys Gln Thr Phe Xaa Xaa Cys Cys Gln
  1               5                  10

<210> SEQ ID NO 5
<211> LENGTH: 13
<212> TYPE: PRT
<213> ORGANISM: Conus geographus
<220> FEATURE:
<221> NAME/KEY: PEPTIDE
<222> LOCATION: (1)..(3)
<223> OTHER INFORMATION: Xaa at residue 1 is Gln or pyro-Glu; Xaa at
      residue 3 is Trp (D or L), neo-Trp or halo-Trp (D or L); Xaa at
      residue 6 is Lys, N-methyl-Lys, N,N-dimethyl-Lys or
      N,N,N-trimethyl-Lys.
<220> FEATURE:
<221> NAME/KEY: PEPTIDE
<222> LOCATION: (7)
<223> OTHER INFORMATION: Xaa at residue 7 is Glu or gamma-carboxy-Glu.

<400> SEQUENCE: 5
```

```
Xaa Gly Xaa Cys Cys Xaa Xaa Asn Ile Ala Cys Cys Ile
 1               5                  10

<210> SEQ ID NO 6
<211> LENGTH: 10
<212> TYPE: PRT
<213> ORGANISM: Conus quercinus

<400> SEQUENCE: 6

Gly Cys Cys Ala Arg Leu Thr Cys Cys Val
 1               5                  10

<210> SEQ ID NO 7
<211> LENGTH: 12
<212> TYPE: PRT
<213> ORGANISM: Conus purpurascens
<220> FEATURE:
<221> NAME/KEY: PEPTIDE
<222> LOCATION: (5)..(6)
<223> OTHER INFORMATION: Xaa at residue 5 is Pro or hydroxy-Pro; Xaa at
      residue 6 is Lys, N-methyl-Lys, N,N-dimethyly-Lys or
      N,N,N-trimethyl-Lys.

<400> SEQUENCE: 7

Asn Gly Cys Cys Xaa Lys Gln Met Arg Cys Cys Thr
 1               5                  10

<210> SEQ ID NO 8
<211> LENGTH: 15
<212> TYPE: PRT
<213> ORGANISM: Conus imperialis
<220> FEATURE:
<221> NAME/KEY: PEPTIDE
<222> LOCATION: (2)..(15)
<223> OTHER INFORMATION: Xaa at residues 2 and 15 is Trp (D or L),
      neo-Trp or halo-Trp (D or L); Xaa at residue 8 is Lys,
      N-methyl-Lys, N,N-dimethyl-Lys or N,N,N-trimethyl-Lys; Xaa at
      residues 10 and 14 is Pro or hydroxy-Pro.

<400> SEQUENCE: 8

Asp Xaa Asn Ser Cys Cys Gly Xaa Asn Xaa Gly Cys Cys Xaa Xaa
 1               5                  10                  15

<210> SEQ ID NO 9
<211> LENGTH: 13
<212> TYPE: PRT
<213> ORGANISM: Conus geographus
<220> FEATURE:
<221> NAME/KEY: PEPTIDE
<222> LOCATION: (1)..(6)
<223> OTHER INFORMATION: Xaa at residue 1 is Gln or pyro-Glu; Xaa at
      residue 2 is Trp (D or L), neo-Trp or halo-Trp (D
      or L); Xaa at residue 6 is Lys, N-methyl-Lys,
      N,N,-dimethyl-Lys or N,N,N-trimethyl-Lys.
<220> FEATURE:
<221> NAME/KEY: PEPTIDE
<222> LOCATION: (7)
<223> OTHER INFORMATION: Xaa at residue 7 is Glu or gamma-carboxy-Glu.

<400> SEQUENCE: 9

Xaa Gly Xaa Cys Cys Xaa Xaa Asn Ile Arg Cys Cys Val
 1               5                  10

<210> SEQ ID NO 10
<211> LENGTH: 15
<212> TYPE: PRT
<213> ORGANISM: Conus textile
<220> FEATURE:
<221> NAME/KEY: PEPTIDE
```

```
<222> LOCATION: (1)..(13)
<223> OTHER INFORMATION: Xaa at residues 1 and 4 is Glu or
      gamma-carboxy-Glu; Xaa at residue 7 is Trp (D or
      L), neo-Trp or halo-Trp (D or L); Xaa at residue
      13 is Pro or hydroxy-Pro.

<400> SEQUENCE: 10

Xaa Cys Cys Xaa Asp Gly Xaa Cys Cys Thr Ala Ala Xaa Leu Thr
 1               5                  10                  15

<210> SEQ ID NO 11
<211> LENGTH: 15
<212> TYPE: PRT
<213> ORGANISM: Conus textile
<220> FEATURE:
<221> NAME/KEY: PEPTIDE
<222> LOCATION: (4)..(13)
<223> OTHER INFORMATION: ; Xaa at residue 4 is Glu or gamma-carboxy-Glu;
      Xaa at residue 7 is Trp (D or L) neo-Trp or
      halo-Trp (D or L); Xaa at residue 13 is Pro or
      hydroxy-Pro.

<400> SEQUENCE: 11

Gly Cys Cys Xaa Asp Gly Xaa Cys Cys Thr Ala Ala Xaa Leu Thr
 1               5                  10                  15

<210> SEQ ID NO 12
<211> LENGTH: 20
<212> TYPE: PRT
<213> ORGANISM: Conus marmoreus
<220> FEATURE:
<221> NAME/KEY: PEPTIDE
<222> LOCATION: (14)..(17)
<223> OTHER INFORMATION: Xaa at residue 14 and 17 is Glu or
      gamma-carboxy-Glu; Xaa at residue 16 is Lys,
      N-methyl-Lys, N,N-dimethyl-Lys or
      N,N,N-trimethyl-Lys.

<400> SEQUENCE: 12

Asn Gly Cys Cys Arg Ala Gly Asp Cys Cys Ser Arg Phe Xaa Ile Xaa
 1               5                  10                  15

Xaa Asn Asp Phe
            20

<210> SEQ ID NO 13
<211> LENGTH: 10
<212> TYPE: PRT
<213> ORGANISM: Conus marmoreus

<400> SEQUENCE: 13

Asn Ala Cys Cys Ile Val Arg Gln Cys Cys
 1               5                  10

<210> SEQ ID NO 14
<211> LENGTH: 11
<212> TYPE: PRT
<213> ORGANISM: Conus marmoreus

<400> SEQUENCE: 14

Asn Gly Cys Cys Arg Ala Gly Asp Cys Cys Ser
 1               5                  10

<210> SEQ ID NO 15
<211> LENGTH: 11
<212> TYPE: PRT
<213> ORGANISM: Conus caracteristicus
<220> FEATURE:
<221> NAME/KEY: PEPTIDE
```

```
<222> LOCATION: (3)
<223> OTHER INFORMATION: Xaa at residue 3 is Pro or hydroxy-Pro.

<400> SEQUENCE: 15

Cys Cys Xaa Arg Arg Leu Ala Cys Cys Ile Ile
  1               5                  10

<210> SEQ ID NO 16
<211> LENGTH: 10
<212> TYPE: PRT
<213> ORGANISM: Conus caracteristicus
<220> FEATURE:
<221> NAME/KEY: PEPTIDE
<222> LOCATION: (3)..(6)
<223> OTHER INFORMATION: Xaa at residue 3 and 6 is Pro or hydroxy-Pro;
      Xaa at residue 5 is Lys, N-methyl-Lys, N,N-dimethyl-Lys or
      N,N,N-trimethyl-Lys.

<400> SEQUENCE: 16

Cys Cys Xaa Asn Xaa Xaa Cys Cys Phe Ile
  1               5                  10

<210> SEQ ID NO 17
<211> LENGTH: 10
<212> TYPE: PRT
<213> ORGANISM: Conus quercinus

<400> SEQUENCE: 17

Gly Cys Cys Ala Met Leu Thr Cys Cys Val
  1               5                  10

<210> SEQ ID NO 18
<211> LENGTH: 13
<212> TYPE: PRT
<213> ORGANISM: Conus gloriamaris
<220> FEATURE:
<221> NAME/KEY: PEPTIDE
<222> LOCATION: (6)..(13)
<223> OTHER INFORMATION: Xaa at residue 6 and 11 is Glu or
      gamma-carboxy-Glu; Xaa at residues 8, 12 and 13 is
      Trp (D or L), neo-Trp or halo-Trp (D or L).

<400> SEQUENCE: 18

Leu Cys Cys Val Thr Xaa Asp Xaa Cys Cys Xaa Xaa Xaa
  1               5                  10

<210> SEQ ID NO 19
<211> LENGTH: 11
<212> TYPE: PRT
<213> ORGANISM: Conus gloriamaris
<220> FEATURE:
<221> NAME/KEY: PEPTIDE
<222> LOCATION: (5)
<223> OTHER INFORMATION: Xaa at residue 5 is Pro or hydroxy-Pro.

<400> SEQUENCE: 19

Val Cys Cys Arg Xaa Val Gln Asp Cys Cys Ser
  1               5                  10

<210> SEQ ID NO 20
<211> LENGTH: 554
<212> TYPE: DNA
<213> ORGANISM: Conus textile
<220> FEATURE:
<221> NAME/KEY: CDS
<222> LOCATION: (65)..(250)

<400> SEQUENCE: 20
```

-continued

```
ggtactcaac gaacttcaag acacattctt ttcacctgga cacgggaagc tgactacaag      60 caga atg tgc tgt ctc cca gtg ttc gtc att ctt ctg ctg att gca          109
     Met Cys Cys Leu Pro Val Phe Val Ile Leu Leu Leu Ile Ala
       1               5                  10                  15 tct gca cct agc gtt gat gcc caa ccg aag acc aaa gat gat gtg ccc      157
Ser Ala Pro Ser Val Asp Ala Gln Pro Lys Thr Lys Asp Asp Val Pro
             20                  25                  30 ctg gca cct ttg cac gat aat gca aag agt gca cta caa cat ttg aac      205
Leu Ala Pro Leu His Asp Asn Ala Lys Ser Ala Leu Gln His Leu Asn
         35                  40                  45 caa cgc tgc tgc caa aca ttc tat tgg tgc tgt gtt caa ggg aaa          250
Gln Arg Cys Cys Gln Thr Phe Tyr Trp Cys Cys Val Gln Gly Lys
     50                  55                  60 tgaatttgga tgagacccct gcgaactgtc catggatgtg agatttggaa agcagactgt    310
tcctttcgca cgtgttcgtg gaattttgaa tggtcgttaa caacacgctg ccacttgcaa   370
gctactatct ctctgtcctt tcatctgtgg aactggatga cctaacaact gaaatatcat   430
agaaattttt cagtgggtat acactatgac catgtagtca gtaattacat catttggacc   490
ttttgaaata tttttcaaaa tgttaagatt ttccccccng gaaaggnctt ttgaagtaaa   550
tatt                                                                 554
```

<210> SEQ ID NO 21
<211> LENGTH: 62
<212> TYPE: PRT
<213> ORGANISM: Conus textile

<400> SEQUENCE: 21

```
Met Cys Cys Leu Pro Val Phe Val Ile Leu Leu Leu Ile Ala Ser
  1               5                  10                  15

Ala Pro Ser Val Asp Ala Gln Pro Lys Thr Lys Asp Asp Val Pro Leu
             20                  25                  30

Ala Pro Leu His Asp Asn Ala Lys Ser Ala Leu Gln His Leu Asn Gln
         35                  40                  45

Arg Cys Cys Gln Thr Phe Tyr Trp Cys Cys Val Gln Gly Lys
     50                  55                  60
```

<210> SEQ ID NO 22
<211> LENGTH: 416
<212> TYPE: DNA
<213> ORGANISM: Conus geographus
<220> FEATURE:
<221> NAME/KEY: CDS
<222> LOCATION: (1)..(183)

<400> SEQUENCE: 22

```
atg tgc tgt ctc cca gtc ttc gtc att ctt ctg ttg ctg att aca tct       48
Met Cys Cys Leu Pro Val Phe Val Ile Leu Leu Leu Leu Ile Thr Ser
  1               5                  10                  15 gca cct agc gtt gat gct cta ccg aag acc agg gat gat gtg ccc cta      96
Ala Pro Ser Val Asp Ala Leu Pro Lys Thr Arg Asp Asp Val Pro Leu
             20                  25                  30 gca tct ttc cac ggt gga tat aat gca agg aga atc cta caa agg cgt     144
Ala Ser Phe His Gly Gly Tyr Asn Ala Arg Arg Ile Leu Gln Arg Arg
         35                  40                  45 cag ggc tgg tgc tgc aaa gaa aat att gcg tgc tgt ata tagtggtaac      193
Gln Gly Trp Cys Cys Lys Glu Asn Ile Ala Cys Cys Ile
     50                  55                  60 gggaaatgac tttggatgag acccctgcaa actgtccctg gatgtgaaat tggaaagta   253
```

```
gactgttcct ttcgcgcgtg ttcgtggaat ttcaaatggt cgtcaacaac acactgctac    313
ttgcaaagct actatctctc tgtcctttca tctgtggaac tgggtgatct aacagctgaa    373
atgtcgcaga aattttttcaa ttggtctata ctatgaccat gta                     416
```

<210> SEQ ID NO 23
<211> LENGTH: 61
<212> TYPE: PRT
<213> ORGANISM: Conus geographus

<400> SEQUENCE: 23

```
Met Cys Cys Leu Pro Val Phe Val Ile Leu Leu Leu Ile Thr Ser
 1               5                  10                  15

Ala Pro Ser Val Asp Ala Leu Pro Lys Thr Arg Asp Asp Val Pro Leu
            20                  25                  30

Ala Ser Phe His Gly Gly Tyr Asn Ala Arg Arg Ile Leu Gln Arg Arg
        35                  40                  45

Gln Gly Trp Cys Cys Lys Glu Asn Ile Ala Cys Cys Ile
    50                  55                  60
```

<210> SEQ ID NO 24
<211> LENGTH: 413
<212> TYPE: DNA
<213> ORGANISM: Conus quercinus
<220> FEATURE:
<221> NAME/KEY: CDS
<222> LOCATION: (1)..(186)

<400> SEQUENCE: 24

```
atg cgc tgt gtc cca gtc ttc atc att ctt ctg ctg ctg agt cca tct    48
Met Arg Cys Val Pro Val Phe Ile Ile Leu Leu Leu Leu Ser Pro Ser
 1               5                  10                  15 gca cct agc gtt gat gcc cat ccg atg acc aaa gat gat gtg ccc cag    96
Ala Pro Ser Val Asp Ala His Pro Met Thr Lys Asp Asp Val Pro Gln
            20                  25                  30 gca tca ttc cat gat gat gca aag cga acc cta caa gta cct tgg atg    144
Ala Ser Phe His Asp Asp Ala Lys Arg Thr Leu Gln Val Pro Trp Met
        35                  40                  45 aaa cgc ggg tgc tgc gca agg ttg act tgc tgc gtt gga cga            186
Lys Arg Gly Cys Cys Ala Arg Leu Thr Cys Cys Val Gly Arg
    50                  55                  60 taaagggaaa tgactttgga tgagacccct gcgaactgtc cctggatgtg aaatttggac    246
agcagactgc tcctttcgca cgtgttcgtg gaattttgaa tggtcgttaa caacacgctg    306
ccacttgcaa gctattatct ctctgtccct ttatctgtgg aactggataa tctaacaact    366
gaaatgtcat tgaaaatttt caatggatat atattatgat ccatata                 413
```

<210> SEQ ID NO 25
<211> LENGTH: 62
<212> TYPE: PRT
<213> ORGANISM: Conus quercinus

<400> SEQUENCE: 25

```
Met Arg Cys Val Pro Val Phe Ile Ile Leu Leu Leu Leu Ser Pro Ser
 1               5                  10                  15

Ala Pro Ser Val Asp Ala His Pro Met Thr Lys Asp Asp Val Pro Gln
            20                  25                  30

Ala Ser Phe His Asp Asp Ala Lys Arg Thr Leu Gln Val Pro Trp Met
        35                  40                  45

Lys Arg Gly Cys Cys Ala Arg Leu Thr Cys Cys Val Gly Arg
```

<210> SEQ ID NO 26
<211> LENGTH: 435
<212> TYPE: DNA
<213> ORGANISM: Conus imperialis
<220> FEATURE:
<221> NAME/KEY: CDS
<222> LOCATION: (26)..(211)

<400> SEQUENCE: 26

```
aattcggaag ctgactacaa gcaga atg tac tgt ctc cca gtc ttc atc att     52
                            Met Tyr Cys Leu Pro Val Phe Ile Ile
                              1               5 ctt ctg ctg ctg att tca tct gca cct agc act cct ccc caa cca agg   100
Leu Leu Leu Leu Ile Ser Ser Ala Pro Ser Thr Pro Pro Gln Pro Arg
 10                  15                  20                  25 aac aaa gat cgt gtg cac ctg ata tct tta ctc gat aat cac aag caa   148
Asn Lys Asp Arg Val His Leu Ile Ser Leu Leu Asp Asn His Lys Gln
                 30                  35                  40 atc cta caa aga gat tgg aac agt tgc tgt ggg aaa aat cct ggt tgc   196
Ile Leu Gln Arg Asp Trp Asn Ser Cys Cys Gly Lys Asn Pro Gly Cys
             45                  50                  55 tgt cct tgg gga aaa tgactttgga tgagacccct gcaaactgtc cctggatgtg   251
Cys Pro Trp Gly Lys
         60 agatttggaa agcagaccgt ttgtggaatt ttgaatggtc gttaacaaca cgctgccact   311 tgcaagctac aatctctctg tcctttcatc tttggaactg gatgatcaaa caactgaaat   371 gtcatagaaa tttttcaatg ggtatacaat atgtgggcat ttagtcagta attacatcat   431 ttgg                                                                435
```

<210> SEQ ID NO 27
<211> LENGTH: 62
<212> TYPE: PRT
<213> ORGANISM: Conus imperialis

<400> SEQUENCE: 27

```
Met Tyr Cys Leu Pro Val Phe Ile Ile Leu Leu Leu Leu Ile Ser Ser
  1               5                  10                  15

Ala Pro Ser Thr Pro Pro Gln Pro Arg Asn Lys Asp Arg Val His Leu
             20                  25                  30

Ile Ser Leu Leu Asp Asn His Lys Gln Ile Leu Gln Arg Asp Trp Asn
         35                  40                  45

Ser Cys Cys Gly Lys Asn Pro Gly Cys Cys Pro Trp Gly Lys
     50                  55                  60
```

<210> SEQ ID NO 28
<211> LENGTH: 421
<212> TYPE: DNA
<213> ORGANISM: Conus geographus
<220> FEATURE:
<221> NAME/KEY: CDS
<222> LOCATION: (1)..(183)

<400> SEQUENCE: 28

```
atg tgc tgt ctc cca gtc ttc gtc att ctt ctg ttg ctg att aca tct    48
Met Cys Cys Leu Pro Val Phe Val Ile Leu Leu Leu Leu Ile Thr Ser
  1               5                  10                  15 gca cct agc gtt gat gct cta ccg aag acc agg gat gat gtg ccc cta    96
Ala Pro Ser Val Asp Ala Leu Pro Lys Thr Arg Asp Asp Val Pro Leu
             20                  25                  30
```

-continued

```
gca tct ttc cac ggt gga tat aat gca agg aga atc cta caa agg cgt       144
Ala Ser Phe His Gly Gly Tyr Asn Ala Arg Arg Ile Leu Gln Arg Arg
         35                  40                  45 cag ggc tgg tgc tgc aaa gaa aat att gcg tgc tgt gta tagtggtaac       193
Gln Gly Trp Cys Cys Lys Glu Asn Ile Ala Cys Cys Val
     50                  55                  60 gggaaatgac tttggatgag acccctgcaa actgtccctg gatgtgaaat ttggaaagta    253
gactgttcct ttcgcgcgtg ttcgtggaat ttcaaatggt cgtcaacaac acactgctac    313
ttgcaaagct actatctctc tgtcctttca tctgtggaac tgggtgatct aacagctgaa    373
atgtcgcaga aatttttcaa ttggtctata ctatgaccat gtagtcag                 421

<210> SEQ ID NO 29
<211> LENGTH: 61
<212> TYPE: PRT
<213> ORGANISM: Conus geographus

<400> SEQUENCE: 29

Met Cys Cys Leu Pro Val Phe Val Ile Leu Leu Leu Leu Ile Thr Ser
  1               5                  10                  15

Ala Pro Ser Val Asp Ala Leu Pro Lys Thr Arg Asp Asp Val Pro Leu
             20                  25                  30

Ala Ser Phe His Gly Gly Tyr Asn Ala Arg Arg Ile Leu Gln Arg Arg
         35                  40                  45

Gln Gly Trp Cys Cys Lys Glu Asn Ile Ala Cys Cys Val
     50                  55                  60

<210> SEQ ID NO 30
<211> LENGTH: 431
<212> TYPE: DNA
<213> ORGANISM: Conus textile
<220> FEATURE:
<221> NAME/KEY: CDS
<222> LOCATION: (1)..(201)

<400> SEQUENCE: 30 atg cgc tgt ttc cca gtc ttc atc att ctt ctg ctg cta att gca tct       48
Met Arg Cys Phe Pro Val Phe Ile Ile Leu Leu Leu Leu Ile Ala Ser
  1               5                  10                  15 gca cct tgc ttt gat gcc cga acg aag acc gat gat gat gtg ccc ctg       96
Ala Pro Cys Phe Asp Ala Arg Thr Lys Thr Asp Asp Asp Val Pro Leu
             20                  25                  30 tca tct ctc cgc gat aat cta aag cga acg ata cga aca cgc ctg aac      144
Ser Ser Leu Arg Asp Asn Leu Lys Arg Thr Ile Arg Thr Arg Leu Asn
         35                  40                  45 ata cgc gag tgc tgc gag gat gga tgg tgc tgt act gct gca ccc tta      192
Ile Arg Glu Cys Cys Glu Asp Gly Trp Cys Cys Thr Ala Ala Pro Leu
     50                  55                  60 aca ggt cgt tagggataaa ggaaaatggc tttggatgag acccctgcga              241
Thr Gly Arg
 65 attgtccctg gatgtgagat ttggaaagca gactgttcct ttcgcacgtg ttcgtggaat    301 ttcgaatggt cgttaacaac acgctgccac ttgcaagcca ccatctctct gtcctttcgt    361 atgtggaact gtatgatcta acaactgaaa tgtcagaaag ttttcagtgg gtatacacta    421 tgatcgtata                                                           431

<210> SEQ ID NO 31
<211> LENGTH: 67
```

<212> TYPE: PRT
<213> ORGANISM: Conus textile

<400> SEQUENCE: 31

Met Arg Cys Phe Pro Val Phe Ile Ile Leu Leu Leu Ile Ala Ser
1               5                   10                  15

Ala Pro Cys Phe Asp Ala Arg Thr Lys Thr Asp Asp Asp Val Pro Leu
            20                  25                  30

Ser Ser Leu Arg Asp Asn Leu Lys Arg Thr Ile Arg Thr Arg Leu Asn
        35                  40                  45

Ile Arg Glu Cys Cys Glu Asp Gly Trp Cys Cys Thr Ala Ala Pro Leu
50                  55                  60

Thr Gly Arg
65

<210> SEQ ID NO 32
<211> LENGTH: 441
<212> TYPE: DNA
<213> ORGANISM: Conus textile
<220> FEATURE:
<221> NAME/KEY: CDS
<222> LOCATION: (1)..(201)

<400> SEQUENCE: 32 atg cgc tgt ttc cca gtc ttc atc att ctt ctg ttg cta att gca tct      48
Met Arg Cys Phe Pro Val Phe Ile Ile Leu Leu Leu Ile Ala Ser
1               5                   10                  15 gca cct tgc ttt gat gcc cga acg aag acc gat gat gat gtg ccc ctg      96
Ala Pro Cys Phe Asp Ala Arg Thr Lys Thr Asp Asp Asp Val Pro Leu
            20                  25                  30 tca tct ctc cgc gat aat cta aag cga acg ata cga aca cgc ctg aac     144
Ser Ser Leu Arg Asp Asn Leu Lys Arg Thr Ile Arg Thr Arg Leu Asn
        35                  40                  45 ata cgc ggg tgc tgc gag gat gga tgg tgc tgt act gct gca ccc tta     192
Ile Arg Gly Cys Cys Glu Asp Gly Trp Cys Cys Thr Ala Ala Pro Leu
50                  55                  60 aca ggt cgt tagggataaa ggaaaatggc tttggatgag acccctgcaa              241
Thr Gly Arg
65 attgtccctg gatgtgagat ttggaaagca gactgttcct ttcgcacgtg ttcgtggaat    301 ttcgaatggt cgttaacaac acgctgccac ttgcaagcca ccatctctct gtcctttcgt    361 atgtggaact gtatgatcta acaactgaaa tgtcagaaag ttttcagtgg gtatacacta    421 tgatcgtata gtcagtaatt                                                441

<210> SEQ ID NO 33
<211> LENGTH: 67
<212> TYPE: PRT
<213> ORGANISM: Conus textile

<400> SEQUENCE: 33

Met Arg Cys Phe Pro Val Phe Ile Ile Leu Leu Leu Ile Ala Ser
1               5                   10                  15

Ala Pro Cys Phe Asp Ala Arg Thr Lys Thr Asp Asp Asp Val Pro Leu
            20                  25                  30

Ser Ser Leu Arg Asp Asn Leu Lys Arg Thr Ile Arg Thr Arg Leu Asn
        35                  40                  45

Ile Arg Gly Cys Cys Glu Asp Gly Trp Cys Cys Thr Ala Ala Pro Leu
50                  55                  60

Thr Gly Arg
65

<210> SEQ ID NO 34
<211> LENGTH: 416
<212> TYPE: DNA
<213> ORGANISM: Conus marmoreus
<220> FEATURE:
<221> NAME/KEY: CDS
<222> LOCATION: (1)..(210)

<400> SEQUENCE: 34

```
atg cgc tgc ctc cca gtc ttc gtc att ctt ctg ctg ctg att gca tct       48
Met Arg Cys Leu Pro Val Phe Val Ile Leu Leu Leu Leu Ile Ala Ser
 1               5                  10                  15 gca cct agc gtt gat gcc cga ccg aag acc aaa gat gat atg ccc ctg       96
Ala Pro Ser Val Asp Ala Arg Pro Lys Thr Lys Asp Asp Met Pro Leu
             20                  25                  30 gca tct ttc cat gat aat gca aag cga atc ctg caa ata ctt cag gac      144
Ala Ser Phe His Asp Asn Ala Lys Arg Ile Leu Gln Ile Leu Gln Asp
         35                  40                  45 aga aat ggt tgc tgc aga gca gga gac tgc tgt tca cga ttt gag ata      192
Arg Asn Gly Cys Cys Arg Ala Gly Asp Cys Cys Ser Arg Phe Glu Ile
     50                  55                  60 aag gaa aat gac ttt gga tgagacccct gcaaactgtc cttggatgtg             240
Lys Glu Asn Asp Phe Gly
 65                  70 agatttggaa agcagactgt tcctttcgca cgtgttcgtg gaatttcgaa tggtcgttaa    300
caacacgctg ccacttgcaa gctactatct ctctgtcctt ttgtctgtgg aactgtatga    360
tcaaacaact gaaatgtcat agaaattttt cagtgggtaa acactatgac catgta        416
```

<210> SEQ ID NO 35
<211> LENGTH: 70
<212> TYPE: PRT
<213> ORGANISM: Conus marmoreus

<400> SEQUENCE: 35

```
Met Arg Cys Leu Pro Val Phe Val Ile Leu Leu Leu Leu Ile Ala Ser
 1               5                  10                  15

Ala Pro Ser Val Asp Ala Arg Pro Lys Thr Lys Asp Asp Met Pro Leu
             20                  25                  30

Ala Ser Phe His Asp Asn Ala Lys Arg Ile Leu Gln Ile Leu Gln Asp
         35                  40                  45

Arg Asn Gly Cys Cys Arg Ala Gly Asp Cys Cys Ser Arg Phe Glu Ile
     50                  55                  60

Lys Glu Asn Asp Phe Gly
 65                  70
```

<210> SEQ ID NO 36
<211> LENGTH: 487
<212> TYPE: DNA
<213> ORGANISM: Conus marmoreus
<220> FEATURE:
<221> NAME/KEY: CDS
<222> LOCATION: (3)..(179)

<400> SEQUENCE: 36

```
ga atg cgc tgc ctc cca gtc ttc gtc att ctt ctg ctg ctg att gca       47
   Met Arg Cys Leu Pro Val Phe Val Ile Leu Leu Leu Leu Ile Ala
    1               5                  10                  15 tct gca cct agc gtt gat gcc cga ccg aag acc aaa gat gat atg ccc      95
```

```
Ser Ala Pro Ser Val Asp Ala Arg Pro Lys Thr Lys Asp Asp Met Pro
                20                  25                  30 ctg gca tct ttc cac gat aat gca aag cga atc ctg caa ata ctt cag      143
Leu Ala Ser Phe His Asp Asn Ala Lys Arg Ile Leu Gln Ile Leu Gln
            35                  40                  45 gac aga aat gct tgc tgc ata gta agg cag tgc tgt tgatgatttg           189
Asp Arg Asn Ala Cys Cys Ile Val Arg Gln Cys Cys
        50                  55 agataaagga aaatgacttt ggatgagacc cctgcaaact gtccctggat gtgagatttg    249
gaaagcagac tgttcctttc gcacgtgttc gtggaatttc gaatggtcgt taacaacacg    309
ctgccacttg caagctacta tctctctgtc ctttcatctg tggaactgta tgatcaaaca    369
actgaaatgt catagaaatt tttcagtggg taaacactat gatcatgtag tcagtaatta    429
catcatttgg aattccatca agcttatcga taccgtcgac ctcgaggggg ggcccggt      487

<210> SEQ ID NO 37
<211> LENGTH: 59
<212> TYPE: PRT
<213> ORGANISM: Conus marmoreus

<400> SEQUENCE: 37

Met Arg Cys Leu Pro Val Phe Val Ile Leu Leu Leu Ile Ala Ser
 1               5                  10                  15

Ala Pro Ser Val Asp Ala Arg Pro Lys Thr Lys Asp Asp Met Pro Leu
                20                  25                  30

Ala Ser Phe His Asp Asn Ala Lys Arg Ile Leu Gln Ile Leu Gln Asp
            35                  40                  45

Arg Asn Ala Cys Cys Ile Val Arg Gln Cys Cys
        50                  55

<210> SEQ ID NO 38
<211> LENGTH: 370
<212> TYPE: DNA
<213> ORGANISM: Conus marmoreus
<220> FEATURE:
<221> NAME/KEY: CDS
<222> LOCATION: (1)..(180)

<400> SEQUENCE: 38 atg cgc tgc ctc cca gtc ttt gtc att ctt ctg ctg ctg att gca tct      48
Met Arg Cys Leu Pro Val Phe Val Ile Leu Leu Leu Leu Ile Ala Ser
 1               5                  10                  15 gca cct agc gtt gat gcc cga ccg aag acc aaa gat gat atg ccc ctg      96
Ala Pro Ser Val Asp Ala Arg Pro Lys Thr Lys Asp Asp Met Pro Leu
                20                  25                  30 gca tct ttc cat gat aat gca aag cga atc ctg caa ata ctt cag gac      144
Ala Ser Phe His Asp Asn Ala Lys Arg Ile Leu Gln Ile Leu Gln Asp
            35                  40                  45 aga aat ggt tgc tgc aga gca gga gac tgc tgt tca tgatttgaga           190
Arg Asn Gly Cys Cys Arg Ala Gly Asp Cys Cys Ser
        50                  55                  60 taaagggaaa tgactttgga tgagacccct gcaaactgtc cttggatgtg agatttggaa    250
agcagactgt tccttcgca cgtgttcgtg gaatttcgaa tggtcgttaa caacacgctg     310
ccacttgcaa gctactatct ctctgtcctt tcatctgtgg aactgtatga tcaaacaact    370

<210> SEQ ID NO 39
<211> LENGTH: 60
<212> TYPE: PRT
<213> ORGANISM: Conus marmoreus
```

<400> SEQUENCE: 39

Met Arg Cys Leu Pro Val Phe Val Ile Leu Leu Leu Ile Ala Ser
1               5                   10                  15

Ala Pro Ser Val Asp Ala Arg Pro Lys Thr Lys Asp Met Pro Leu
            20                  25                  30

Ala Ser Phe His Asp Asn Ala Lys Arg Ile Leu Gln Ile Leu Gln Asp
        35                  40                  45

Arg Asn Gly Cys Cys Arg Ala Gly Asp Cys Cys Ser
    50                  55                  60

<210> SEQ ID NO 40
<211> LENGTH: 413
<212> TYPE: DNA
<213> ORGANISM: Conus caracteristicus
<220> FEATURE:
<221> NAME/KEY: CDS
<222> LOCATION: (1)..(192)

<400> SEQUENCE: 40 atg cgc tgt ctc ccg gtc ttc atc att ctt ctg ctg att gca tct       48
Met Arg Cys Leu Pro Val Phe Ile Ile Leu Leu Leu Ile Ala Ser
1               5                   10                  15 gca cct ggc gtt gat gcc caa ccg aag acc aaa tat aat gcg ccc ctg   96
Ala Pro Gly Val Asp Ala Gln Pro Lys Thr Lys Tyr Asn Ala Pro Leu
            20                  25                  30 aca tct ctc cac gat aat gca aag ggt ata cta caa gaa cat tgg aac   144
Thr Ser Leu His Asp Asn Ala Lys Gly Ile Leu Gln Glu His Trp Asn
        35                  40                  45 aaa cgc tgc tgc ccc aga agg ctt gcc tgc tgt att ata gga cgg aaa   192
Lys Arg Cys Cys Pro Arg Arg Leu Ala Cys Cys Ile Ile Gly Arg Lys
    50                  55                  60 tgaatgattt tgggtgagat ccctgcaaac tgtccctgga tttgaatttt ggaaagcaga   252
ctgttccttt cgcacgtgtt cgtggaattt cgaatggtcg ttaacaacac gctgccactt   312
gcaagctact atctctctgt ccttttctc tgtgaaactg gatggtctaa caactgaaat    372
gtcatagaaa attttcaatg ggtatactct atgaccatct a                       413

<210> SEQ ID NO 41
<211> LENGTH: 64
<212> TYPE: PRT
<213> ORGANISM: Conus caracteristicus

<400> SEQUENCE: 41

Met Arg Cys Leu Pro Val Phe Ile Ile Leu Leu Leu Ile Ala Ser
1               5                   10                  15

Ala Pro Gly Val Asp Ala Gln Pro Lys Thr Lys Tyr Asn Ala Pro Leu
            20                  25                  30

Thr Ser Leu His Asp Asn Ala Lys Gly Ile Leu Gln Glu His Trp Asn
        35                  40                  45

Lys Arg Cys Cys Pro Arg Arg Leu Ala Cys Cys Ile Ile Gly Arg Lys
    50                  55                  60

<210> SEQ ID NO 42
<211> LENGTH: 410
<212> TYPE: DNA
<213> ORGANISM: Conus caracteristicus
<220> FEATURE:
<221> NAME/KEY: CDS
<222> LOCATION: (1)..(189)

<400> SEQUENCE: 42

```
atg cgc tgt ctc cca gtc ttc atc att ctt ctg ctg ctg att gca tct      48
Met Arg Cys Leu Pro Val Phe Ile Ile Leu Leu Leu Ile Ala Ser
 1               5                  10                  15 gca cct ggc gtt gat gcc caa ccg aag acc aaa tat gat gcg ccc ctg      96
Ala Pro Gly Val Asp Ala Gln Pro Lys Thr Lys Tyr Asp Ala Pro Leu
             20                  25                  30 aca tct ctc cac gat aat gca aag ggt ata cta caa gaa cat tgg aac     144
Thr Ser Leu His Asp Asn Ala Lys Gly Ile Leu Gln Glu His Trp Asn
         35                  40                  45 aaa cgc tgc tgc ccc aac aag cct tgc tgt ttt ata gga agg aaa         189
Lys Arg Cys Cys Pro Asn Lys Pro Cys Cys Phe Ile Gly Arg Lys
     50                  55                  60 tgaatgattt tgggtgagac ccctgcaaac tgtccctgga tttgaatttt ggaaagcaga   249
ctgttccttt cgcacgtgtt cgtggaattt cgaatggtcg ttaacaacac gctgccactt   309
gcaagctact atctctctgt cctttttctc tgtgaaactg gatggtctaa caactgagat   369
gtcatagaaa attttcaatc ggtgtactct atgaccatct a                      410
```

<210> SEQ ID NO 43
<211> LENGTH: 63
<212> TYPE: PRT
<213> ORGANISM: Conus caracteristicus

<400> SEQUENCE: 43

```
Met Arg Cys Leu Pro Val Phe Ile Ile Leu Leu Leu Ile Ala Ser
 1               5                  10                  15

Ala Pro Gly Val Asp Ala Gln Pro Lys Thr Lys Tyr Asp Ala Pro Leu
             20                  25                  30

Thr Ser Leu His Asp Asn Ala Lys Gly Ile Leu Gln Glu His Trp Asn
         35                  40                  45

Lys Arg Cys Cys Pro Asn Lys Pro Cys Cys Phe Ile Gly Arg Lys
     50                  55                  60
```

<210> SEQ ID NO 44
<211> LENGTH: 413
<212> TYPE: DNA
<213> ORGANISM: Conus quercinus
<220> FEATURE:
<221> NAME/KEY: CDS
<222> LOCATION: (1)..(186)

<400> SEQUENCE: 44

```
atg cgc tgt gtc cca gtc ttc atc att ctt ctg ctg ctg agt cca tct      48
Met Arg Cys Val Pro Val Phe Ile Ile Leu Leu Leu Ser Pro Ser
 1               5                  10                  15 gca cct agc gtt gat gcc cat ccg atg acc aaa gat gat gta ccc cag      96
Ala Pro Ser Val Asp Ala His Pro Met Thr Lys Asp Asp Val Pro Gln
             20                  25                  30 gca tct ctc cat gat gat gca aag cga acc cta caa gta cct tgg atg     144
Ala Ser Leu His Asp Asp Ala Lys Arg Thr Leu Gln Val Pro Trp Met
         35                  40                  45 aaa cgc ggg tgc tgc gca atg ttg act tgc tgc gtt gga cga             186
Lys Arg Gly Cys Cys Ala Met Leu Thr Cys Cys Val Gly Arg
     50                  55                  60 taaagggaaa tgactttgga tgagacccct acgaactgtc cctggatgtg aaatttggac   246
agcagactgc tccttcgca cgtgttcgtg gaatttcgaa tggtcgttaa caacacgctg    306
ccacttgcaa gctattatct ctctgtccct ttatctgtgg aactgataa tctaacaact    366
```

```
gaaacgtcat tgaaaatttt caatggatat atattatgat ccatata         413
```

```
<210> SEQ ID NO 45
<211> LENGTH: 62
<212> TYPE: PRT
<213> ORGANISM: Conus quercinus

<400> SEQUENCE: 45

Met Arg Cys Val Pro Val Phe Ile Ile Leu Leu Leu Ser Pro Ser
 1               5                  10                  15

Ala Pro Ser Val Asp Ala His Pro Met Thr Lys Asp Asp Val Pro Gln
                20                  25                  30

Ala Ser Leu His Asp Asp Ala Lys Arg Thr Leu Gln Val Pro Trp Met
            35                  40                  45

Lys Arg Gly Cys Cys Ala Met Leu Thr Cys Cys Val Gly Arg
        50                  55                  60
```

```
<210> SEQ ID NO 46
<211> LENGTH: 735
<212> TYPE: DNA
<213> ORGANISM: Conus gloriamaris
<220> FEATURE:
<221> NAME/KEY: CDS
<222> LOCATION: (70)..(258)

<400> SEQUENCE: 46
gggcaggtac tcaacgaact tcaggacaca ttcttttcac ctggacacgg gaaactgact      60 ataagcaga atg cgc tac cta cca gtc ttc gtc att ctt ctg ctg ctg att     111
          Met Arg Tyr Leu Pro Val Phe Val Ile Leu Leu Leu Leu Ile
            1               5                  10 gca tct ata cct agc gat act gtc caa ctg aag acc aaa gat gat atg      159
Ala Ser Ile Pro Ser Asp Thr Val Gln Leu Lys Thr Lys Asp Asp Met
 15                  20                  25                  30 ccc ctg gca tct ttc cac ggt aat gga aga cga atc ctg cga atg ctt      207
Pro Leu Ala Ser Phe His Gly Asn Gly Arg Arg Ile Leu Arg Met Leu
                35                  40                  45 tca aac aaa cgc tta tgc tgt gtc acc gag gat tgg tgc tgt gaa tgg      255
Ser Asn Lys Arg Leu Cys Cys Val Thr Glu Asp Trp Cys Cys Glu Trp
            50                  55                  60 tgg taaaggaaaa tgactttgga tgagacccct gcaaactgtt tctggatgtg           308
Trp agatttggaa agcagactgt tctttcgcac gtattcgtga atttcgaat ggtcgttaac      368 aacacgctgc cacttgcaag ctgctatctc tctgtctttt catctgtgga actgtatgat    428
ctaacaactg aaatgtcata gcatttttc attgggtata cactatgacc atgtagccag      488
taattacatc atttggacct tttggatatt tttcagtatg taagtgtgtt cccttaaaaa    548
gtcctttgta attatgtatt ttaanaattt angttttgca cataaattgt aaaacgctgt    608
cctttctgtt gntcctacat cantggtggg gaaaagnaaa atgtttggcc ntggtcaaat   668
ttaaataatn accctgccgt ttnaatgcng ttattantgg tattttnaac nttgnacggt   728
taaactt                                                               735
```

```
<210> SEQ ID NO 47
<211> LENGTH: 63
<212> TYPE: PRT
<213> ORGANISM: Conus gloriamaris

<400> SEQUENCE: 47

Met Arg Tyr Leu Pro Val Phe Val Ile Leu Leu Leu Leu Ile Ala Ser
```

```
                    1               5                  10                  15
Ile Pro Ser Asp Thr Val Gln Leu Lys Thr Lys Asp Asp Met Pro Leu
                   20                  25                  30

Ala Ser Phe His Gly Asn Gly Arg Arg Ile Leu Arg Met Leu Ser Asn
           35                  40                  45

Lys Arg Leu Cys Cys Val Thr Glu Asp Trp Cys Cys Glu Trp Trp
       50                  55                  60
```

<210> SEQ ID NO 48
<211> LENGTH: 374
<212> TYPE: DNA
<213> ORGANISM: Conus gloriamaris
<220> FEATURE:
<221> NAME/KEY: CDS
<222> LOCATION: (3)..(188)

<400> SEQUENCE: 48

```
ga atg cgc tgt ctc cca gtc ttc gtc att ctt ctg ctg att gca          47
   Met Arg Cys Leu Pro Val Phe Val Ile Leu Leu Leu Ile Ala
     1               5                  10                  15 tct gca cct agc gtt gat gcc caa ccg aag acc aaa gat gat gtg ccc     95
Ser Ala Pro Ser Val Asp Ala Gln Pro Lys Thr Lys Asp Asp Val Pro
                   20                  25                  30 ctg gca cct ttg cac gat aat ata agg agt act cta caa aca ctt cgg    143
Leu Ala Pro Leu His Asp Asn Ile Arg Ser Thr Leu Gln Thr Leu Arg
           35                  40                  45 aag aaa gtc tgc tgc cgc cca gtg cag gat tgc tgt tca ggg aaa        188
Lys Lys Val Cys Cys Arg Pro Val Gln Asp Cys Cys Ser Gly Lys
       50                  55                  60 tgaagggaaa tgaatttgga tgagacccct gcgaactgtc cctggatgtg agatttggaa    248
agcagactgt tcctttcgca cgtgttcgtg gaatttcgaa tggtcgttaa caacacgctg    308
ccacttgcaa gctactatct ctctgtcctt tcatctgcgg aactggatga cctaaagctt    368
gtgatc                                                               374
```

<210> SEQ ID NO 49
<211> LENGTH: 62
<212> TYPE: PRT
<213> ORGANISM: Conus gloriamaris

<400> SEQUENCE: 49

```
Met Arg Cys Leu Pro Val Phe Val Ile Leu Leu Leu Ile Ala Ser
  1               5                  10                  15

Ala Pro Ser Val Asp Ala Gln Pro Lys Thr Lys Asp Asp Val Pro Leu
               20                  25                  30

Ala Pro Leu His Asp Asn Ile Arg Ser Thr Leu Gln Thr Leu Arg Lys
           35                  40                  45

Lys Val Cys Cys Arg Pro Val Gln Asp Cys Cys Ser Gly Lys
       50                  55                  60
```